United States Patent [19]

Evans et al.

[11] Patent Number: 5,602,009
[45] Date of Patent: Feb. 11, 1997

[54] DOMINANT NEGATIVE CHIMERAS OF THE STEROID/THYROID SUPERFAMILY OF RECEPTORS

[75] Inventors: Ronald M. Evans, La Jolla, Calif.; Stanley M. Hollenberg, Seattle, Wash.; Anthony E. Oro, San Diego, Calif.; Klaus Damm, Munich, Germany; Richard A. Heyman, Encinitas, Calif.

[73] Assignee: The Salk Institute for Biological Studies, La Jolla, Calif.

[21] Appl. No.: 777,232

[22] PCT Filed: May 25, 1990

[86] PCT No.: PCT/US90/03113

§ 371 Date: May 10, 1993

§ 102(e) Date: May 10, 1993

Related U.S. Application Data

[63] Continuation-in-part of Ser. No. 358,696, May 26, 1989, abandoned, which is a continuation-in-part of Ser. No. 289,561, Dec. 23, 1988, abandoned.

[51] Int. Cl.$^6$ .................................................. C12N 15/62
[52] U.S. Cl. .................. 435/69.7; 435/252.3; 435/320.1; 530/350; 536/23.4
[58] Field of Search ................................ 435/69.7, 257.3, 435/320.1; 530/350; 536/23.4

[56] References Cited

U.S. PATENT DOCUMENTS 4,818,684  4/1989  Edelman et al. ..................... 435/172.3

FOREIGN PATENT DOCUMENTS

WO88/03168  5/1988  WIPO .

OTHER PUBLICATIONS

Adler et al., "Steroid Receptor–Mediated Inhibition of Rat Prolactin Gene Expression Does Not Require the Receptor DNA–Binding Domain" *Cell* 52:685–695 (1988).
Nature 330:624–629, 17 Dec. 1987, Gigisene et al Identification of a receptor for the morphogen retilore acids.
Akerblom et al., "Negative Regulation by Glucocorticoids Through Interference with cAMP Responsive Enhancer" *Science* 241:350–353 (1988).
Anderson and Axel, "A Bipotential Neuroendocrine Precursor Whose Choice of Cell Fate Is Determined by NGF and Glucocorticoids" *Cell* 47:1079–1090 (1986).
Berg, Jeremy M., "DNA Binding Specificity of Steroid Receptors" *Cell* 57:1065–1068 (1989).
Brent et al., "Thyroid Hormone Aporeceptor Represses T3–Inducible Promoters and Blocks Activity of the Retinoic Acid Receptor" *The New Biologist* 1(3):329–336 (1989).
Brent and Ptashne, "A Eukaryotic Transcriptional Activator Bearing the DNA Specificity of a Prokaryotic Repressor" *Cell* 43:729–736 (1985).
Clark et al., "Pharmaceuticals from transgenic livestock" *Tibtech* 5:20–24 (1987).

Damm et al., "Protein encoded by v–erbA functions as a thyroid–hormone receptor antagonist" *Nature* 339(6226):593–597 (1989).
Damm et al., "A single point mutation in erbA restores the erythroid transforming potential of a mutant avian erythroblastosis virus (AEV) defective in both erbA and erbB oncogenes" *EMBO J.* 6(2):375–382 (1987).
Danielsen et al., "Domains of the Glucocorticoid Receptor Involved in Specific and Nonspecific Deoxyribonucleic Acid Binding, Hormone Activation, and Transcriptional Enhancement" *Mol. Endo.* 1(11):816–822 (1987).
Delegeane et al., "Tissue–Specific Enhancer of the Human Glycoprotein Hormone α–Subunit Gene: Dependence on Cyclic AMP–Inducible Elements" *Molecular and Cellular Biol.* 7(11):3994–4002 (1987).
deWet et al., "Firefly Luciferase Gene: Structure and Expression in Mammalian Cells" *Molecular and Cellular Biol.* 7(2):725–737 (1987).
Espeseth et al., "Retinoic acid receptor expression vector inhibits differentiation of F9 embryonal carcinoma cells" *Genes & Development* 3:1647–1656 (1989).
Evans, Ronald M., "The Steroid and Thyroid Hormone Receptor Superfamily" *Science* 240:889–895 (1988).
Evans and Hollenberg, "Zinc Fingers: Gilt by Association" *Cell* 52:1–3 (1988).
Giguere et al., "Functional Domains of the Human Glucocorticoid Receptor" *Cell* 46:645–652 (1986).
Glass et al., "The Thyroid Hormone Receptor Binds with Opposite Transcriptional Effects to a Common Sequence Motif in Thyroid Hormone and Estrogen Response Elements" *Cell* 54:313–323 (1988).
Glass et al., "A c–erb–A binding site in rat growth hormone gene mediates trans–activation by thyroid hormone" *Nature* 329:738–741 (1987).
Godowski et al., "Signal Transduction and Transcriptional Regulation by Glucocorticoid Receptor–LexA Fusion Proteins" *Science* 241:812–816 (1988).
Graupner et al., "Dual regulatory role for thyroid–hormone receptors allows control of retinoic–acid receptor activity" *Nature* 340:653–656 (1989).
Green and Chambon, "Oestradiol induction of a glucocorticoid–responsive gene by a chimaeric receptor" *Nature* 325:74–78 (1987).
Gronemeyer et al., "The chicken progesterone receptor: sequence, expression and functional analysis" *EMBO J.* 6:3985–3994 (1987).

(List continued on next page.)

Primary Examiner—John Ulm
Attorney, Agent, or Firm—Pretty, Schroeder, Brueggemann & Clark; Stephen E. Reiter; Robert T. Ramos

[57] ABSTRACT

Disclosed are novel trans-repressing analog receptors wherein the ligand-binding domain(s) are modified versus wild type receptor, such novel receptors having repressed trans-activation transcription activation properties. Also disclosed are recombinant methods and means for preparing such receptors and assays using such receptors.

20 Claims, 13 Drawing Sheets

OTHER PUBLICATIONS

Herskowitz, Ira, "Functional inactivation of genes by dominant negative mutations" *Nature* 329:219–222 (1987).

Hollenberg and Evans, "Multiple and Cooperative Trans–Activation Domains of the Human Glucocorticoid Receptor" *Cells* 55:899–906 (1988).

Hollenberg et al., "Colocalization of DNA–Binding and Transcriptional Activation Functions in the Human Glucocorticoid Receptor" *Cell* 49:39–46 (1987).

Hope et al., "Structural and functional characterizations of the short acidic transcriptional activation region of yeast GCN4 protein" *Nature* 333:635–640 (1988).

Hope and Struhl, "Functional Dissection of a Eukaryotic Transcriptional Activator Protein, GCN4 of Yeast" *Yeast* 46:885–894 (1986).

Hu and Gudas, "Cyclic AMP Analogs and Retinoic Acid Influence the Expression of Retinoic Acid Receptor α, β, and γ mRNAs in F9 Teratocarcinoma Cells" *Molecular and Cellular Biol.* 10(1):391–396 (1990).

Kumar et al., "Functional Domains of the Human Estrogen Receptor" *Cell* 51:941–951 (1987).

Lavin et al., "The Thyroid Hormone Receptor Binds to Multiple Domains of the Rat Growth Hormone 5'–Flanking Sequence" *Journal of Biol. Chem.* 263:9418–9426 (1988).

Lech et al., "DNA–Bound Fos Proteins Activate Transcription in Yeast" *Cell* 52:179–184 (1988).

Ma and Ptashne et al., "A New Class of Yeast Transcriptional Activators" *Cell* 51:113–119 (1987).

Ma and Ptashne, "Deletion Analysis of GAL4 Defines Two Transcriptional Activating Segments" *Cell* 48:847–853 (1987).

Miesfeld et al., "Glucocorticoid Receptor Mutants That Define a Small Region Sufficient for Enhancer Activation" *Science* 236:423–427 (1987).

Oro et al., "Transcriptional Inihibition by a Glucocorticoid Receptor–β–Galactosidase Fusion Protein" *Cell* 55:1109–1114 (1989).

Ptashne, Mark, "How eukaryotic transcriptional activators work" *Nature* 335:683–689 (1988).

Sakai et al., "Hormone–mediated repression: a negative glucocorticoid response element from the bovine prolactin gene" *Genes & Development* 2:114–1154 (1988).

Sap et al, "A c–erb–A protein is a high–affinity receptor for thyroid hormone" *Nature* 324:635–640 (1986).

Schule et al., "Many Transcription Factors Interact Synergistically with Steroid Receptors" *Science* 242:1418–1420 (1988).

Sigler Paul B., "Acid blobs and negative noodles" *Nature* 333:210–212 (1988).

Stein et al., "The Induction of a Neural–Specific Gene, SCG10, by Nerve Growth Factor in PC12 Cells Is Transcriptional, Protein Synthesis Dependant, and Glucocorticoid Inhibitable" *Developmental Biology* 127:316–325 (1988).

Thierry and Yaniv, "The BPV1–E2 trans–acting protein can be either an activator or a repressor of the HPV18 regulatory region" *EMBO J.* 6(11):3391–3397 (1987).

Thompson and Evans, "Trans–activation by thyroid hormone receptors: Functional parallels with steroid hormone receptors" *Proc. Natl. Acad. Sci. USA* 86:3494–3498 (1989).

Thompson et al., "Identification of a Novel Thyroid Hormone Receptor Expressed in the Mammalian Central Nervous System" *Science* 237:1610–1614 (1987).

Tora et al., "The N–terminal region of the chicken progesterone receptor specifies target gene activation" *Nature* 333:185–188 (1988).

Tsai et al., "Molecular Interactions of Steroid Hormone Receptor with Its Enhancer Element: Evidence for Receptor Dimer Formation" *Cell* 55:361–369 (1988).

Umesono and Evans, "Determinants of Target Gene Specificity for Steroid/Thyroid Hormone Receptors" *Cell* 57:1139–1146 (1989).

Vennstrom et al., "Molecular Cloning of the Avian Erythroblastosis Virus Genome and Recovery of Oncogenic Virus by Transfection of Chicken Cells" *J. of Virology* 36(2):575–585 (1980).

Waterman et al., "A Single Domain of the Estrogen Receptor Confers Deoxyribonucleic Acid Binding and Transcriptional Activation of the Rat Prolactin Gene" *Molecular Endocrinology* 2(1):14–21 (1988).

Weinberger et al., "The c–erb–A gene encodes a thyroid receptor" *Nature* 324 (6098):641–646 (1986).

Yu et al., "A naturally immunogenic virion–associated protein specific for HIV–2 and SIV" *Nature* 335:262–265 (1988).

FIG.1-1

```
(-171) CGG GGG GCG GAA CAG CCA AGG GCG GAG CCA GGG CAC GCG GGT CAG GCC CCT    -121
       Arg Gly Ala Glu Gln Pro Arg Ala Glu Pro Gly His Ala Gly Gln Ala Pro
                                       -50                                GAG →

CCG GCC CTG ACT GAC TGG GCA AGG ATC AAG ACA GAG CCA GAG CTT GCG AGT ACT GGT CCG CCC    -1
       Pro Ala Leu Thr Asp Trp Ala Arg Ile Lys Thr Glu Pro Glu Leu Ala Ser Thr Gly Pro Pro
                                   -30                           ERB A →

GTG GCC ATG GTA CCT GTA GTG ATT AAG GAG GAG CCC GCT TGG ACC CCT CTG GAG CCA
       Val Ala Met Pro Val Val Ile Lys Glu Glu Pro Ala Trp Thr Pro Leu Glu Pro
       -20                          -10

GAG ACT CGG TGG CTG GAT GGC TAC ATC CTT AAA AGA AAG CAA CAG AGC AGC AAG GAT GAA CAG CTG CTG CTG    120
       Glu Thr Arg Trp Leu Asp Gly Tyr Ile Leu Lys Arg Lys Gln Ser Ser Lys Asp Glu Gln
                                                  10                              20

AGC ATG TCA GGG TAC ATC CCT AGC TAC TCC TAC ATC ACC TGC GAG GGC TGC AAG AGC TTT    240
       Ser Met Ser Gly Tyr Ile Pro Ser Tyr Ser Tyr Ile Thr Cys Glu Gly Cys Lys Ser Phe
                                          30                              40                       60

GGG GAC AAA GCC ACC ATC CAG AAG CTG AAC CTG GAC TAC CGC TAC ACG TGC CGG GAG TGC AAG TAC GAT GGG TGC    240
       Gly Asp Lys Ala Thr Ile Gln Lys Leu Asn Leu Asp Tyr Arg Tyr Thr Cys Arg Glu Cys Lys Tyr Asp Gly Cys
                                                              50                              70                       80

TTC CGT CGG ACC ATC CAG AAG AAC CTG CAC CCC ACC TAC TCC TGC CAG CTG TGC CGC TTC AAG AAG TGC ATC
       Phe Arg Arg Thr Ile Gln Lys Asn Leu His Pro Thr Tyr Ser Cys Gln Leu Cys Arg Phe Lys Lys Cys Ile
                                                      70                              90                            100

TGC GTC ATC GAC AAG ATC ACC CGC AAC CAG TGC CAG CTG TGC CGC TTC AAG AAG TGC ATC
       Cys Val Ile Asp Lys Ile Thr Arg Asn Gln Cys Gln Leu Cys Arg Phe Lys Lys Cys Ile

TCC GTG ATG GCC ATG GAC CTG GTG CTG GAC GAC TCG AAG CGG GTA GCC AAG CGG AAG    360
       Ser Val Gly Met Ala Met Asp Leu Val Leu Asp Asp Ser Lys Arg Val Ala Lys Arg Lys
                                              110                               120
```

FIG.1-2

```
CTG ATC GAG GAG AAC CGG GAG CGA AAG GAG ATG ATC AAA TCC CTG CAG CAC
Leu Ile Glu Glu Asn Arg Glu Arg Lys Glu Met Ile Lys Ser Leu Gln His
                                     130                         140

CGG CCC AGC CCC AGC GCA GAG GAG CTG TGG ATC CAC GTG ACC GAG GCG CGC      480
Arg Pro Ser Pro Ser Ala Glu Glu Leu Trp Ile His Val Thr Glu Ala Arg
                    150                         160

AGC ACC AAC GCG CAG CAG CAC AGC GGC AAA TTC CTC GAA GAT ATC
Ser Thr Asn Ala Gln Gln His Ser Gly Lys Phe Leu Glu Asp Ile
                        170                         180

GGT CAG TCG CCC ATG GCC TCC ATG CTT GAC AAA GTG GAC CTG GAG GCG TTC AGC
Gly Gln Ser Pro Met Ala Ser Met Leu Asp Lys Val Asp Leu Glu Ala Phe Ser
                        190                         200                 600
└── DOMAIN 1              ┌── DOMAIN 2

GAG TTT ACA AAA ATC ATC ACG GCC ATC ACC CGC GTC GAC TTT GCC AAA AAC CTG
Glu Phe Thr Lys Ile Ile Thr Ala Ile Thr Arg Val Asp Phe Ala Lys Asn Leu
                210                         220

CCC ATG TTC TCG GAG CTG CCG TGC GAG CTG GAG ATC ATC CTG AAG GGC TGC TGC ATC
Pro Met Phe Ser Glu Leu Pro Cys Glu Leu Glu Ile Ile Leu Lys Gly Cys Cys Met
            230                         240                              720

GAG ATC ATG TCG CTG CGC TCG CTG CGC GCC GTG GAT CAG TAC GAC CCC GAA ACG CTG ACG CTG
Glu Ile Met Ser Leu Arg Ser Leu Arg Ala Val Asp Gln Tyr Asp Pro Glu Thr Leu Thr Leu
                250                         260

AGC GGG GAA ATG GCC GTC AAA CGC GAG CAG TTG AAG AAC GGA CTG GGG GTC TCT
Ser Gly Glu Met Ala Val Lys Arg Glu Gln Leu Lys Asn Gly Leu Gly Val Ser
        270                         280                                  840

GAT GCC ATC TTC GAC CTC GGC AAG TCG CTG TCT GCC TTC AAC CTG GAC GAC ACC GAG GTG
Asp Ala Ile Phe Asp Leu Gly Lys Ser Leu Ser Ala Phe Asn Leu Asp Asp Thr Glu Val
                290                         300
```

FIG.1-3

```
GCC CTG CTG CAG GCC GTG CTG CTC ATG TCC TCA GAC CGG ACG GGG CTG ATC TGC GTG CAT      960
Ala Leu Leu Gln Ala Val Leu Leu Met Ser Ser Asp Arg Thr Gly Leu Ile Cys Val Asp
                                    310                                     320
AAG ATA GAG AAG TGC CAG GAG TCG TAC CTG GCG TTC GAG CAC TAC ATC AAC TAC CGC
Lys Ile Glu Lys Cys Gln Glu Ser Tyr Leu Ala Phe Glu His Tyr Ile Asn Tyr Arg
                                    330                                     340
AAA CAC AAC ATT CCC CAC TTC TGG TCC AAG CTG ATC AAG GTG GCG GAC CTG CGC ATG         1080
Lys His Asn Ile Pro His Phe Trp Ser Lys Leu Ile Lys Val Ala Asp Leu Arg Met
                                    350                                     360
ATC GGC GCC TAC CAC CCC AGC CGC TTC CTG CAC ATG AAG GTG GAG TGC CCC ACG GAG CTC
Ile Gly Ala Tyr His Pro Ser Arg Phe Leu His Met Lys Val Glu Cys Pro Thr Glu Leu
                                    370                                     380
CCC CCA AGG AGG TGT AGA GCC CTA CAG ATT TTG GGA AGT ATA TTG CCC TTT GTA TAG TCC     1200
Pro Pro Arg Arg Cys Arg Ala Leu Gln Ile Leu Gly Ser Ile Leu Pro Phe Val AM
                                    390

ATCCTACAAGAGCAAAAACTTGTAAGCATTTCAGGTAGCAAAGTAATGAAACCACACAAAATGCTGAAAATGCTCCACAGT
TGAATGCACAGATATTTATCTTCTGTGTTTATTCCTGAAGTGTAAGGAATCATAGATTACTTGTTTCTTT             1359
```

DOMINANT NEGATIVE CHIMERAS OF THE STEROID/THYROID SUPERFAMILY OF RECEPTORS

RELATED APPLICATIONS

This is a continuation-in-part application of U.S. patent application Ser. No. 07/358,696, filed 26 May 1989, now abandoned, which is in turn, a continuation-in-part application of U.S. patent application Ser. No. 07/289,561 filed 23 Dec. 1988, now abandoned, the entire contents of which are both hereby incorporated by express reference herein.

FIELD OF THE INVENTION

The present invention relates to trans-repressing analog receptors of the steroid/thyroid superfamily. In a particular aspect, it relates to the identification and characterization of proteins that function as transcription trans-activation repressors, as well as to their preparation and use, including novel DNA isolates encoding same; expression vectors operatively harboring these DNA sequences; and hosts transfected with said vectors.

In another aspect, the present invention relates to the use of the above-described transcription trans-activation repressors in various assays and screening methods.

BACKGROUND OF THE INVENTION

The characterization and preparation of various hormone and hormone-like receptors, including steroid, thyroid, and retinoid receptors such as those represented by the glucocorticoid, mineralocorticoid, thyroid, estrogen-related and retinoid classes has been subject of considerable research.

It is known, for example, that the glucocorticoid receptor belongs to a large superfamily of ligand-dependent transcription factors that have themselves diverse roles in homeostasis, growth and development. Comparison of complementary DNAs encoding these receptors, as well as mutational analyses of their coding sequences, have identified certain functional domains within the molecule that are thought responsible respectively for DNA binding, hormone binding and nuclear localization. See Evans, et al., *Science* 240, 889 (1988) for a review of this subject matter.

In the case of the glucocorticoid receptor, the so-called DNA binding domain spans some sixty-six amino acids and is highly conserved among various species. In addition, this domain has been found to be required in order to activate transcription. See Hollenberg, et al., *Cell* 49, 39 (1987), Miesfeld, et al., *Science* 236, 423 (1987), Danielsen, et al., *Mol.Endo* 1, 816 (1987), Kumar, et al., *Cell* 51, 941 (1987), Gronemeyer, *EMBO J.* 6, 3985 (1987), and Waterman, et al., *Mol.Endo* 2, 14 (1988). This domain has been found to contain nine invariant cysteine residues. Although the contribution of each cysteine residue to overall function is unknown, as is the actual structure formed by this domain, it has been proposed that these cysteine residues coordinate two zinc ions to form two DNA binding, so-called finger domains, which result in a ternary structure thought responsible for the localization and binding of the glucocorticoid receptor to the requisite DNA site. See Klug, et al., *Tr.Biochem.Sci* 12, 464 (1987), Bens, et al., *Cell* 52, 1 (1988), and Evans, supra.

In a location nearer the carboxyl-terminal end distal from the DNA binding region is the so-called ligand binding domain which has the demonstrated ability to block activity of the receptor in the absence of hormone. Thus, presence of the requisite hormone relieves the inhibition of the receptor to activity. Deletion of this region has been found to produce a hormone-independent transcription activator. See Godowski, et al., *Nature* 325, 365 (1987), Hollenberg, et al., supra, Kumar, et al., supra, Danielsen et al., supra, and Adler et al., *Cell,* 52, 685 (1988).

In contrast to these two domains, the sequences lying towards the amino-terminal region from the DNA binding domain are poorly understood both as to structure, and particularly, function. This region is extremely variable both in size and in composition amongst the various receptors— See Evans, supra—and may contribute to the heterogeneity of receptor function. See Kumar et al., supra, and Tora et al., 333, 185 (1988).

Despite extensive analysis, some of which has been reported in the scientific literature, the region(s) that determine(s) trans-activation of transcription initiation remains poorly characterized. Trans-activation domains can be defined as polypeptide regions that, when combined with the functional DNA binding domain, increase productive transcription initiation by RNA polymerases. See Sigler, *Nature* 333, 210 (1988), Brent et al., *Cell* 43, 729 (1985), Hope et al., *Cell* 46, 885 (1986), Ma et al., *Cell* 48, 847 (1987), Ma et al., *Cell* 51, 113 (1987), Lech et al., *Cell* 52, 179 (1988), and Hope et al., *Nature* 333, 635 (1988).

Previous research of the human glucocorticoid receptor by linker scanning mutagenesis identified two regions outside of the DNA binding region having a role in transcription activation. These regions were defined as $T_1$ and $T_2$. Giguere et al., *Cell* 46, 645 (1986). Further research from these laboratories has also resulted in the report of a co-localization of trans-activation and DNA binding functions. See Hollenberg et al., supra, Miesfeld, et al., supra, Danielsen et al., supra, and Waterman et al., supra. As a result, this research has given rise to an emerging picture of an increasingly modular molecule with discrete domains, each contributing to the identified properties of ligand-binding, DNA-binding and trans-activation of transcription. Until recently, the region(s) determining the trans-activation activity were not at all well understood. Thus, the picture based upon extant literature lacks an overall appreciation of the dynamic nature of the steroid receptors and how the various domains determine the cascade of events initiated by ligand-binding and consummated by promoter-specific trans-activation.

Further, although previous research has identified functional "domains", there has been little systematic effort to identify amino acids that contribute to the specific activities of the molecule itself. Thus, the previous identification of steroid receptor trans-activation regions resulted only from a demonstrated loss of activity via deletion or insertional mutagenesis, but in no case have the properties of the regions themselves been confirmed in assays that reflect a dominant gain of function. See also Ptashne, *Nature* 335, 683 (1988).

Thus, Godowski et al., *Science* 241, 812 (1988), report results that show that the glucocorticoid receptor contains at least one "enhancement domain" other than that overlapping the glucocorticoid response element binding region (i.e., the DNA binding domain) and that the second domain occupies a region near the receptor amino-terminus. Similarly, Webster et al., *Cell* 54, 199 (1988) report on an inducible transcription activation function of the estrogen and glucocorticoid receptors, and these researchers speculate that the relative positions of the hormone regions (i.e., ligand and DNA-binding domains) are not important for the transcription induction activity of the receptor. Yet, these researchers admit that they have no definition of the exact location and nature of what they call the hormone-inducible activating domain, to say nothing of its characterization and role in trans-activating potential.

The work by Giguere et al., supra, demonstrated a loss of activity in the glucocorticoid receptor based upon an assay measuring transcription activity, as a result of performing random site-mutagenesis at several locations of the molecule. As a follow-up, Hollenberg et al. deleted regions in the molecule, again demonstrating overall loss of transcription activity induced by such removal of stretches of amino acids.

The human glucocorticoid receptor (hGR) has served as a prototype, model receptor for gene regulation. As noted above, the DNA-binding and ligand-binding functional domains have been defined previously. Similarly, it has been found that these modular domains of the hGR receptor or other receptors may be moved to other parts of the receptor or attached to heterologous DNA-binding domains and still maintain function.

In contrast, relatively little is known about negative regulation by hGR. This is surprising in light of the key role that steroids play in development and negative feedback regulation. Glucocorticoid helps determine neural crest cell fate in the developing sympathoadrenal system, in part by repressing the induction of neural-specific genes [See Stein et al., *Dev Bio* 127, 316 (1988) and Anderson et al, *Cell* 47, 1079 (1986)]. Glucocorticoid also modulates the hypothalamic-pituitary-adrenal axis by inhibiting second messenger-induced peptide hormone induction. Recently, Akerblom et al. (*Science* 241, 350 (1988)) showed that the hGR negatively regulates the cyclic AMP-inducible alpha glycoprotein hormone promoter in asteroid and DNA-binding dependent manner. Wild-type expression is exhibited by a promoter of just 168 base pairs (termed alpha168). Basal expression in placental cells is mediated by factors bound to a 36 base pair palindromic cyclic AMP response element (CRE) cooperating with proteins binding to a 25 base pair tissue-specific element (TSE). Expression may be further enhanced through the CRE by the elevation of intracellular cyclic AMP levels. The hGR represses both the basal and cyclic AMP enhanced transcription in a glucocorticoid-dependent fashion. The transacting elements to which the hGR binds have been defined and are related to the consensus GRE sequence for activation. Similar research is reported by Sakai, et al., *Genes and Development* 2, 1144 (1988).

SUMMARY OF THE INVENTION

The present invention is the result of a thorough analysis of the structural requirements of hormone receptors for repression. This analysis has revealed an absolute requirement for the DNA binding domain and a role for the carboxyl terminus for repression. Although the DNA-binding domain alone is not sufficient for maximal repression, the addition of polypeptides to the carboxyl terminus or other modifications as described herein at the carboxyl terminus leads to the creation of novel fusion proteins having dominant negative repressor activity.

In accordance with the present invention, we have identified, isolated and characterized the domains of intracellular hormone or hormone-like receptors that can be modified so as to repress trans-activation transcription activity. This information has enabled the further characterization of various receptors of the steroid/thyroid superfamily, both in terms of physical attributes and biological function and effect of various domains, particularly that domain capable of being modified to provide repressed transcription activity. The foregoing has in turn enabled the production of novel analog receptors having repressed transcription activation properties.

It has been determined, based upon the information provided herein, that receptors of the steroid/thyroid superfamily contain domains that function in overall trans-activation transcription activity, even though the three receptor domains, i.e., the DNA-binding, the ligand-binding, and the trans-activation transcription domains, are positioned independently of one another and are autonomous in function. In accordance with the present invention, it has been discovered that the carboxyl terminus of a given receptor is that domain responsible for modulating the trans-activation transcription activity of said receptor. It has further been found that the DNA-binding domain is a necessary component in any receptor hereof having repressed trans-activation transcription activity.

This invention provides for novel hormone or hormone-like analog receptors wherein the trans-activation transcription activity is repressed. Such novel analog receptors contain a DNA-binding domain, optionally an N-terminal domain and a C-terminal domain that has been altered so as to provide repressed trans-activation transcription activity compared with parental or wild-type receptor. The novel analog receptors hereof may be hybrid receptors wherein the DNA-binding domain, N-terminal domain and C-terminal domain are provided from different sources. For example, the C-terminal domain of the glucocorticoid receptor can be replaced herein by a portion of the C-terminus of the v-erbA protein. Alternatively, the C-terminal domain of the glucocorticoid receptor can be replaced with at least a portion of a polypeptide such as β-galactosidase.

The present invention is further directed to the preparation of such novel analog receptors hereof via recombinant DNA technology in all relevant aspects, including a DNA molecule that is a recombinant DNA molecule or a cDNA molecule consisting of a sequence encoding said analog receptor or a C-terminal modified domain thereof, requisite expression vectors operatively harboring such DNA comprising expression control elements operative in the recombinant hosts selected for the expression, and recombinant host cells transfected with such operative expression vectors.

The present invention is also directed to the use of the novel analog receptors described herein for identifying the response element and/or function of an "orphan" receptor, i.e., a receptor for which the associated response element and/or function is not known.

The present invention is further directed to the use of the novel analog receptors described herein in an improved assay system for the determination of a specific wild type receptor, wherein more than one response element present in the assay system is capable of interacting with the wild type receptor.

An additional utility for such repressed analog receptors hereof lies in the area of cancer therapy. Certain cells require augmented levels of hormone in order to become tumorigenic. One example is the elevated estrogen requirement observed in mammary tumors. Indeed, estrogen antagonists, such as tamoxifin, are used in therapy so as to decrease the amount of estrogen available so that the transformation of normal mammary cells into tumorous cells is inhibited.

Alternatively, the analog receptors of the present invention can be used for such purpose.

BRIEF DESCRIPTION OF THE FIGURES

FIGS. 1-1 to 1-3 provides the amino acid sequence of the v-erbA protein.

FIG. 2 is a dose response curve for hGR-mediated negative regulation.

DETAILED DESCRIPTION OF THE INVENTION

In accordance with the present invention, there is provided a trans-repressing analog receptor of the steroid/thyroid superfamily of receptors, said analog comprising:
  (1) a first amino acid sequence which is a DNA-binding domain, through which said analog is capable of binding to a hormone response element of a wild type receptor, and
  (2) a second amino acid sequence which is positioned at the carboxy-terminal end of the DNA-binding domain, wherein said second sequence is selected from:
    (a) a polypeptide which has at least about 90% as many amino acids as the ligand binding domain of the carboxy-terminal portion of said wild type receptor; wherein said polypeptide has less than about 60% amino acid identity relative to the carboxy-terminal domain of said wild type receptor over either
      (i) the entire length of said polypeptide, if shorter than the carboxy-terminal domain of said wild type receptor, or
      (ii) any of said polypeptide segments having the same length as the carboxy-terminal domain of said wild type receptor; or
    (b) at least the 84 carboxy-terminal amino acids of the carboxy-terminal portion of the v-erbA protein as defined by amino acid numbers 313–398 (see FIG. 1; Note that the erb-A amino acid numbering will vary by about 255 amino acids depending on whether the gag sequence (the amino-terminal 255 amino acids) is included for purposes of numbering the amino acids of the erb-A protein).

In accordance with another embodiment of the present invention, there is (are) provided expression vector(s) operatively harboring DNA molecule(s) which is (are) recombinant DNA molecule(s) or cDNA molecule(s) encoding the above-described receptor analogs; recombinant host cells transfected with such expression vectors; and cell cultures comprising such cells in an extrinsic support medium.

In accordance with yet another embodiment of the present invention, there is provided a non-human transgenic mammal, having disease symptoms due to the inability to respond normally to asteroid or thyroid hormone, said mammal having at least a subset of its cells capable of expressing an analog receptor for one of said hormones, said analog receptor having trans-repression activity greater than that of its corresponding wild type receptor and trans-activation activity less than that of its corresponding wild type receptor.

Figure 2:
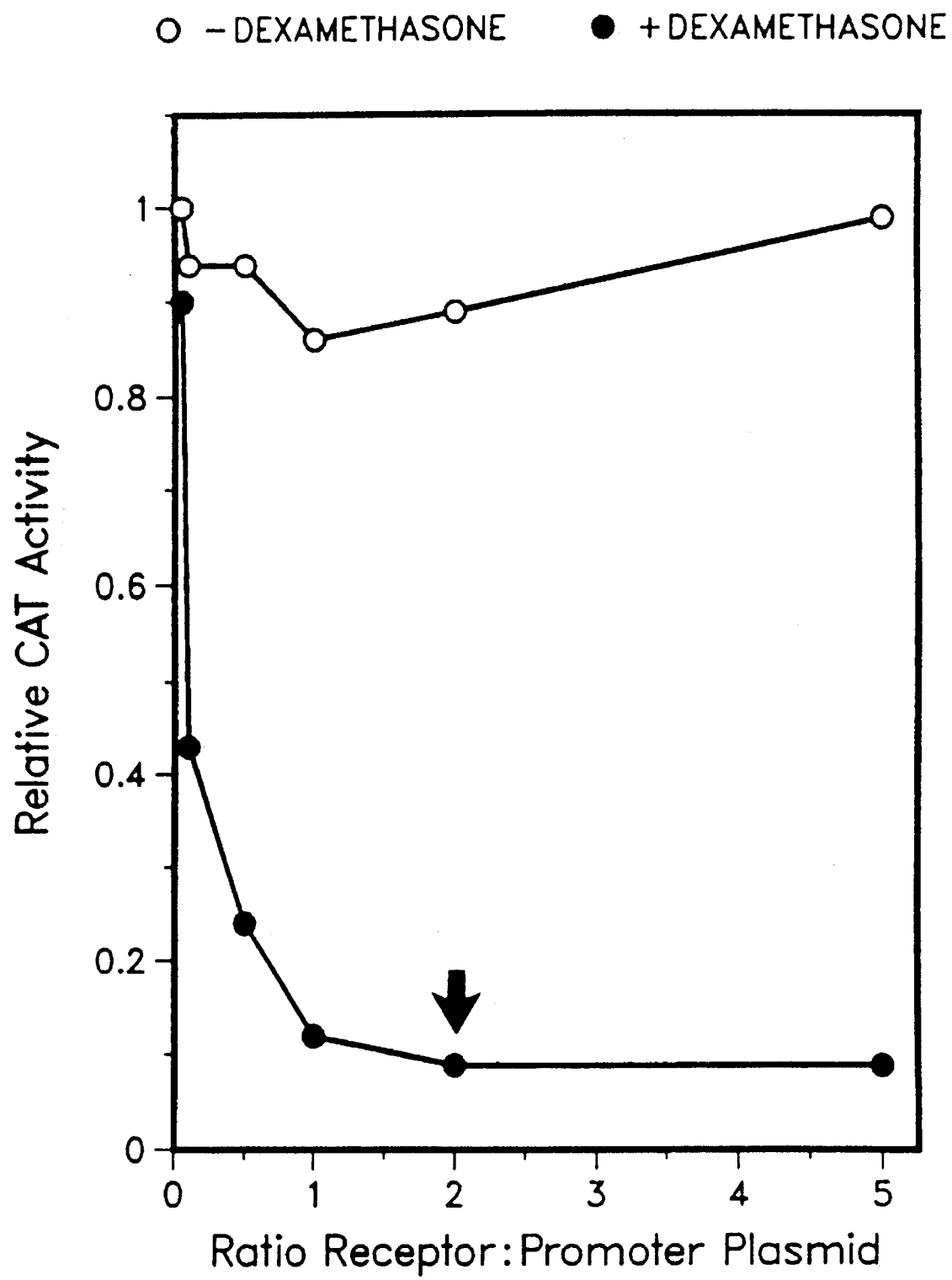

In accordance with still another embodiment of the present invention, there is provided a method for converting a wild type hormone receptor into a trans-repressing analog receptor, said method comprising:
  replacing the ligand binding domain of said wild type receptor with at least the 84 carboxy terminal amino acids of the verbA protein as defined by amino acid numbers 313–398 (see FIGS. 1-1 to 1-3).

This latter embodiment of the present invention can alternatively be accomplished by replacing the ligand binding domain of said wild type receptor with a polypeptide which has at least 90% as many amino acids as at least the ligand binding domain of the carboxy-terminus of said wild type receptor; and wherein said polypeptide has less than about 60% amino acid identity relative to the carboxy-terminus of said wild type receptor over either:
  (i) the entire length of said polypeptide, if shorter than the carboxy-terminus of said wild type receptor, or
  (ii) any segment of said polypeptide having the same length as the carboxy-terminus of said wild type receptor.

In accordance with a further embodiment of the present invention, there is provided a method for blocking the transcriptional activation by a wild type receptor of a hormone response element in a cell by contacting the cell with an effective amount of an analog receptor as described hereinabove.

In accordance with a still further embodiment of the present invention, there is provided a method for blocking the transcriptional activation by a wild type receptor of a hormone response element present in a cell, said method comprising
  (a) substantially deleting the ligand binding domain of said wild type receptor,
  (b) operatively linking the modified receptor of step (a) to at least the 84 carboxy terminal amino acids of the verbA protein as defined by amino acid numbers 313–398 (see FIGS. 1-1 to 1-3) to produce a fusion protein, and thereafter
  (c) contacting said cell with an effective amount of said fusion protein.

This latter embodiment of the present invention can alternatively be accomplished by:
  (a') substantially deleting the ligand binding domain of said wild type receptor;
  (b') operatively linking the modified receptor of step (a') to a polypeptide which has at least about 90% as many amino acids as the ligand binding domain of said wild type receptor, wherein said polypeptide has less than about 60% amino acid identity relative to the ligand binding domain of said wild type receptor over either
    (i) the entire length of said polypeptide, if shorter than the ligand binding domain of said wild type receptor, or (ii) any segment of said polypeptide having the same length as the ligand binding domain of said wild type receptor, to produce a fusion protein, and thereafter (c) contacting said cell with an effective amount of said fusion protein.

In accordance with another embodiment of the present invention, there is provided a method for identifying the response element and/or function of a receptor for which the associated response element and/or function is not known, said method comprising:

comparing the response of a test system having known responsiveness to wild-type receptor to the response of said test system when treated with trans-repressing analog receptor; wherein said trans-repressing analog receptor comprises:

(1) a first amino acid sequence which is a DNA-binding domain, through which said analog is capable of binding to a hormone response element of said wild type receptor, and (2) a second amino acid sequence which is positioned at the carboxy-terminal end of the DNA-binding domain, wherein said sequence is selected from:

(a) a polypeptide which has at least about 90% as many amino acids as the ligand binding domain of the carboxy-terminal portion of said wild type receptor; wherein said polypeptide has less than about 60% amino acid identity relative to the carboxy-terminal domain of said wild type receptor over either:

the entire length of said polypeptide if shorter than the carboxy-terminal domain of said wild type receptor, or any segment of said polypeptide having the same length as the carboxy-terminal domain of said wild type receptor; or (b) at least the 84 carboxy-terminal amino acids of the carboxy-terminal portion of the v-erbA protein as defined by amino acid numbers 313–398 (see FIGS. 1-1 to 1-3).

For example, the specific response element(s) with which the orphan receptor interacts can be determined by screening a variety of test systems, each having a single known response element. The response element of the specific test system which is activated by the orphan receptor, but which is repressed by an analog receptor derived from the orphan receptor according to the present invention, is the response element for the orphan receptor.

Similarly, the function of an orphan receptor can be determined by comparing the response of a test system when contacted with the orphan receptor, relative to the response of the same test system when contacted with a trans-repressing analog of the orphan receptor according to the present invention. Differences in the response in the two side-by-side comparisons provide an indication of the functional role of the orphan receptor.

In accordance with yet another embodiment of the present invention, an improvement is provided for use in assay systems responsive to the presence of a specific wild type receptor, wherein more than one response element is capable of interacting with said wild type receptor, the improvement comprising inactivating, with respect to said assay, response element(s) which also respond to wild type receptor(s) other than said specific receptor; wherein said response elements are inactivated by adding to said assay system an effective amount of a trans-repressing analog receptor for each of said other receptor(s), wherein each of said trans-repressing analog receptors comprises:

(1) a first amino acid sequence which is a DNA-binding domain, through which said analog is capable of binding to a hormone response element of a receptor other than said specific wild type receptor, and (2) a second amino acid sequence which is positioned at the carboxy-terminal end of the DNA-binding domain, wherein said sequence is selected from:

(a) a polypeptide which has at least about 90% as many amino acids as the ligand binding domain of the carboxy-terminal portion of said receptor other than said specific wild type receptor; wherein said polypeptide has less than about 60% amino acid identity relative to the carboxy-terminal domain of said receptor other than said specific wild type receptor over either:

the entire length of said polypeptide if shorter than the carboxy-terminal domain of said receptor other than said specific wild type receptor, or any segment of said polypeptide having the same length as the carboxy-terminal domain of said receptor other than said specific wild type receptor; or (b) at least the 84 carboxy-terminal amino acids of the carboxy-terminal portion of the v-erbA protein as defined by amino acid numbers 313–398 (see FIGS. 1-1 to 1-3).

As employed herein, the term "dominant negative", when used in reference to the analog receptors of the present invention, refers to species which have a negative effect on the transcriptional activation activity of the associated response element, even in the presence of wild-type receptor and its associated ligand.

Amino acid abbreviations employed in the present disclosure use the following standard single- and three-letter designations, i.e.:

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

Receptors employed in the practice of the present invention can be prepared by recombinant techniques, by synthetic chemistry, or the like. The thus produced receptor, in its various forms, is recovered and purified to a level suitable for its intended use.

The existence of a superfamily of ligand-inducible trans-acting factors is now recognized, including those for steroid hormones, retinoic acid and vitamin D3, two subtypes (isoforms) of thyroid hormone receptors (termed $\alpha$ and $\beta$), and the like. Mutational analysis and structural comparisons of these hormone receptors has enabled the identification of domains responsible for hormone-binding, DNA-binding and trans-activation of gene expression. See Sap et al., *Nature* 324, 635 (1986), Weinberger et al., *Nature* 324, 641 (1986) and Evans, *Science* 240, 889 (1988).

The receptors of the present invention are trans-repressing analogs of hormone or hormone-like receptors which are referred to broadly as members of the steroid/thyroid superfamily of receptors, e.g., glucocortoid receptor, mineralocorticoid receptor, progesterone receptor, estrogen receptor, estrogen-related receptors, vitamin $D_3$ receptor, thyroid hormone receptor, retinoic acid receptor, aldosterone receptor, androgen receptor, and the like. Receptors of the present invention include functional equivalents of all of the above, including receptors differing in one or more amino acids from the corresponding parent, or in glycosylation and/or phosphorylation patterns, or in bounded conformational structure. The terminology "functional equivalents thereof" refers to trans-repressing analog receptors which differ from the previously described analog receptor(s) with respect to one or more amino acids, insofar as such differences do not lead to a destruction in kind of the basic repressed receptor activity or biofunctionality.

It will be understood, therefore, that receptors that are known in the art, whether wild-type, hybrids, or functional equivalents as set forth herein, are suitable as starting materials for the practice of the present invention.

As employed herein, the term "expression vector" includes vectors which are capable of expressing DNA sequences contained therein, where such sequences are operatively linked to other sequences capable of effecting their expression. It is implied, although not always explicitly stated, that these expression vectors may be replicable in host organisms either as episomes or as an integral part of the chromosomal DNA. As employed herein, the term "operative," or grammatical equivalents, means that the respective DNA sequences are operational, that is, work for their intended purposes. In sum, "expression vector" is given a functional definition, and any DNA sequence which is capable of effecting expression of a specified DNA sequence disposed therein is included in this term as it is applied to the specified sequence. In general, expression vectors of utility in recombinant DNA techniques are often in the form of "plasmids" which refer to circular double stranded DNA loops which, in their vector form, are not bound to the chromosome. In the present specification, the terms "plasmid" and "vector" are used interchangeably as the plasmid can be a commonly used form of vector. However, the invention is intended to include such other forms of expression vectors which serve equivalent functions and which become known in the art subsequently hereto.

As employed herein, the term "recombinant host cells" refers to cells which have been transfected with vectors constructed using recombinant DNA techniques.

As employed herein, the term "extrinsic support medium" includes those known or devised media that can support cells in a growth phase or maintain them in a viable state such that they can perform their recombinantly harnessed function. See, for example, *ATCC Media Handbook*, Ed. Cote et al., American Type Culture Collection, Rockville, Md. (1984). A growth supporting medium for mammalian cells, for example, preferably contains a serum supplement such as fetal calf serum or other supplementing component commonly used to facilitate cell growth and division such as hydrolysates of animal meat or milk, tissue or organ extracts, macerated clots or their extracts, and so forth. Other suitable medium components include, for example, transferrin, insulin and various metals.

The vectors and methods disclosed herein are suitable for use in host cells over a wide range of prokaryotic and eukaryotic organisms.

In addition to the above discussion and the various references to existing literature teachings, reference is made to standard textbooks of molecular biology that contain definitions and methods and means for carrying out basic techniques encompassed by the present invention. See, for example, Maniatis, et al, *Molecular Cloning: A Laboratory Manual,* Cold Spring Harbor Laboratory, New York, 1982 and the various references cited therein, and in particular, Colowick et al., *Methods in Enzymology Vol* 152, Academic Press, Inc. (1987). All of the herein cited publications are by this reference hereby expressly incorporated herein.

Non-human transgenic organisms contemplated by the present invention include rodents (e.g., mice, rats), pigs, sheep, lower eukaryotes (e.g., Drosophila, Xenopus), and the like.

Transcriptional activation by the steroid receptors and the thyroid hormone receptors has been found to be dependent on the presence and binding of the respective ligand. However, deletion analysis has disclosed that glucocorticoid, estrogen, and progesterone receptors lacking the hormone binding domain still recognize the specific response elements and may function as constitutive activators. Thus, neither the ligand itself nor its binding domain need to participate directly in DNA recognition.

The v-erbA protein has been found to contain an apparently intact DNA-binding domain; however, as a result of amino-acid changes and a deletion in the carboxy-terminal domain (relative to its progenitor, the thyroid hormone receptor), it lacks the ability to bind thyroid hormone. By analogy to mutated steroid hormone receptors, it has been proposed that these mutations, in conjunction with the high level of expression, convert the thyroid hormone receptor into v-erbA, which is a hormone independent transcription factor.

Utilizing a gel retardation assay, it has now been demonstrated that both v-erbA and, the thyroid hormone receptor recognize and bind to a cognate response element in the absence of ligand. The consequence of this binding is the suppression of a thyroid hormone responsive reporter gone by the non-liganded receptor. Addition of thyroid hormone results in a 10–100 fold stimulation of transcription from the repressed level. Surprisingly, v-erbA does not function as an activator as one might expect, but rather as a constitutive repressor of $T_3$ responsive genes. When co-expressed with the thyroid hormone receptor, and in the further presence of thyroid hormone, the v-erbA repression is dominant, blocking hormone stimulated modulation, thereby demonstrating that v-erbA can function as a potent receptor antagonist.

The present invention thus embraces hormone or hormone-like receptor analogs having the ability to repress trans-activation transcription activity of a promoter with which it is associated, or an extrinsic, operative promoter. Such repression is due, for example, to the intrinsic ability of the analog receptor to competitively bind to a DNA response element of said promoter or by the ability of the analog receptor to competitively displace other polypeptide(s) that bind to said DNA response element, or a proximate DNA response element, thus creating an overall repression of trans-activation transcription activity compared with that of its corresponding parent or wild-type receptor.

EXAMPLES

The following experimental details set forth the methodology employed in identifying, characterizing and preparing particular novel analog receptors. The art skilled will recognize that by supplying the present information including the location and makeup of trans-activation transcription repression domain(s) of a given receptor and how such receptor can be manipulated to produce the novel analog receptors hereof having repressed trans-activation transcription activity, it is not necessary, or perhaps scientifically advisable, to repeat the details described herein to reproduce this work. Instead, they may choose to employ alternative, reliable and known methods. For example, they may synthesize the underlying DNA sequences encoding a particular novel receptor hereof for deployment within similar or other suitable, operative expression vectors and culture systems. Thus, in addition to supplying details actually employed, the present disclosure serves to enable reproduction of the specific receptors disclosed, as well as others, and fragments thereof, using means within the skill of the art having benefit of the present disclosure. All of such means are included within the enablement and scope of the present invention.

EXAMPLE 1

Transfections

Transfections in JEG-3 human placental cells are performed via the calcium phosphate precipitation method described by Delegeane et al, *Mol. Cell. Biol.*, Vol. 7, pp. 3994–4002 (1987). JEG-3 cells, maintained in Dulbecco's modified Eagle's medium (DMEM), 10 percent defined calf bovine serum (CBS), and 0.4 percent glucose are split 24 hours prior to transfection into 5 percent CBS charcoal-stripped serum plus glucose (Akerblom et al., *Science* 241, pp. 350–353 (1988)). Typically, 2 µg of reporter plasmid and 4 µg of receptor plasmid were used along with 2 µg of a Rous sarcoma virus (RSV)-β-galactosidase construct (Hollenberg et al., *Cell* 49, pp. 39–46 (1987)) as an internal control for transfection efficiency. Dexamethasone and aldosterone ($10^{-7}$M) were added after calcium phosphate treatment. For the β-galactosidase fusion experiments, the internal control was RSV-luciferase.

Transfections in CV-1 cells are also performed via the calcium phosphate precipitation method. CV-1 cells are maintained in DMEM supplemented with 5% calf bovine serum and transfected at 30%–50% confluency with a total of 20 µg DNA. 5 µg expression plasmid and 2.5 µg reporter plasmid DNA, together with 2.5 µg RSV-β-gal as an internal control for transfection efficiency, are cotransfected per 10 cm dish. Transfected cells are grown in 10% resin-treated fetal calf serum [Samuels et al., *J. Endocrinology*, Vol. 105, pp. 80–85 (1979)] in the presence or absence of $10^{-7}$M 3,5,3' triiodothyronine ($T_3$). Cells are harvested 40 hours after the addition of $T_3$; β-galactosidase and CAT-assays are then performed as described in Example 2.

EXAMPLE 2

Reporter Assays

Chloramphenicol acetyltransferase (CAT) assays are performed as described by Hollenberg, et al, *Cell*, Vol. 49, pp. 39–46 (1987), but with 25 µg of total cell extract protein for 3 hours or less. Thin-layer chromatography (TLC) plates are cut and counted in Econofluor containing 5% dimethyl sulfoxide (DMSO).

β-Galactosidase (β-gal) assays are performed as described by Herbomel, et al. *Cell*, Vol. 29, pp. 653–662 (1984).

EXAMPLE 3 hGR Mediated Negative Regulation

To demonstrate hGR-mediated repression of the alpha168 promoter (a promoter for the alpha-subunit gene encoding chorionic gonadotropin; which is repressed by GR), a dose response study is conducted of negative regulation of the alpha168-CAT reporter plasmid by the hGR expression plasmid in human placental JEG-3 cells. Varying amounts of the hGR expression plasmid (driven by the RSV promoter) and alpha168-CAT (reporter) expression plasmid are cotransfected by the calcium phosphate precipitation method. Cotransfections are carried out so as to provide increasing receptor to promoter ratios. The resultant transient CAT activity in the presence or absence of the steroid hormone dexamethasone is then measured. Throughout the study, the total amount of transfected RSV promoter DNA is kept constant by substituting an RSV control plasmid, thus controlling for possible titration of transcription-factors by RSV DNA. The CAT activity of the reporter construction is measured as described above.

The alpha168-CAT reporter plasmid is constructed as described by Delegeane et al., supra.

The hGR expression plasmid, driven by the RSV promoter, is constructed as described by Hollenberg et al, *Cell*, Vol. 49, pp. 39–46 (1987).

Control plasmid RSV contains the rat thyroid hormone receptor coding region in the antisense direction, and is described by Thompson et al, in *Science*, Vol. 237, pp. 1610–1614 (1987).

FIG. 2 shows the effect of the transfection of hGR cDNA on reporter gene expression in the presence and absence of dexamethasone. Open circles in the Figure indicate media without added dexamethasone, while solid circles indicate media with added dexamethasone ($10^{-7}$M). In the particular experiment presented in FIG. 2, 2 µg of promoter plasmid is used. The arrow indicates the ratio of receptor to promoter used in subsequent experiments.

FIG. 2 shows that increasing amounts of the receptor expression plasmid yield a correspondingly higher steroid-dependent repression. In the absence of receptor cDNA, less than 10 percent of maximal repression is measured. Beginning at a receptor to promoter ratio of 1 and continuing to a ratio of 5, a plateau of repression activity emerges where more receptor plasmid yields no additional steroid-dependent repression. Since the amount of RSV promoter is held constant, this plateau indicates probable saturation of the site of receptor action. For subsequent experiments, a receptor to promoter ratio of 2:1 is used. The steroid-dependent repression varies between 6 and 20 fold with an average of 9 fold as typified in FIG. 2. This assay can reliably measure as low as 10 percent of wild type hGR repression.

Figure 3A:
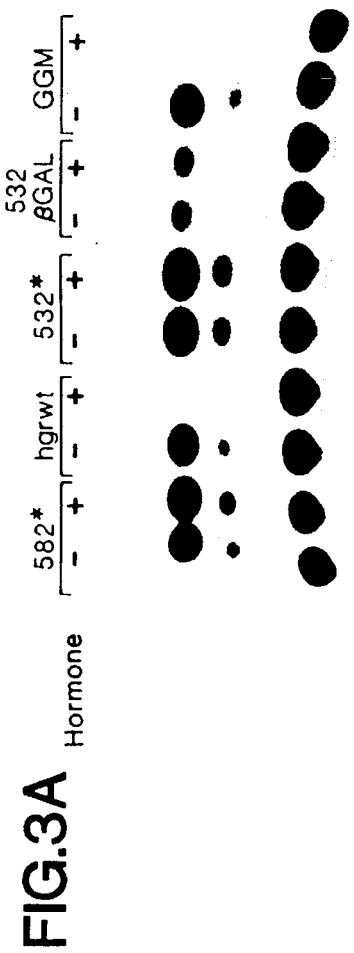
FIGS. 3A and 3B illustrate the repression by carboxyl terminal fusion proteins.
Figure 3B:
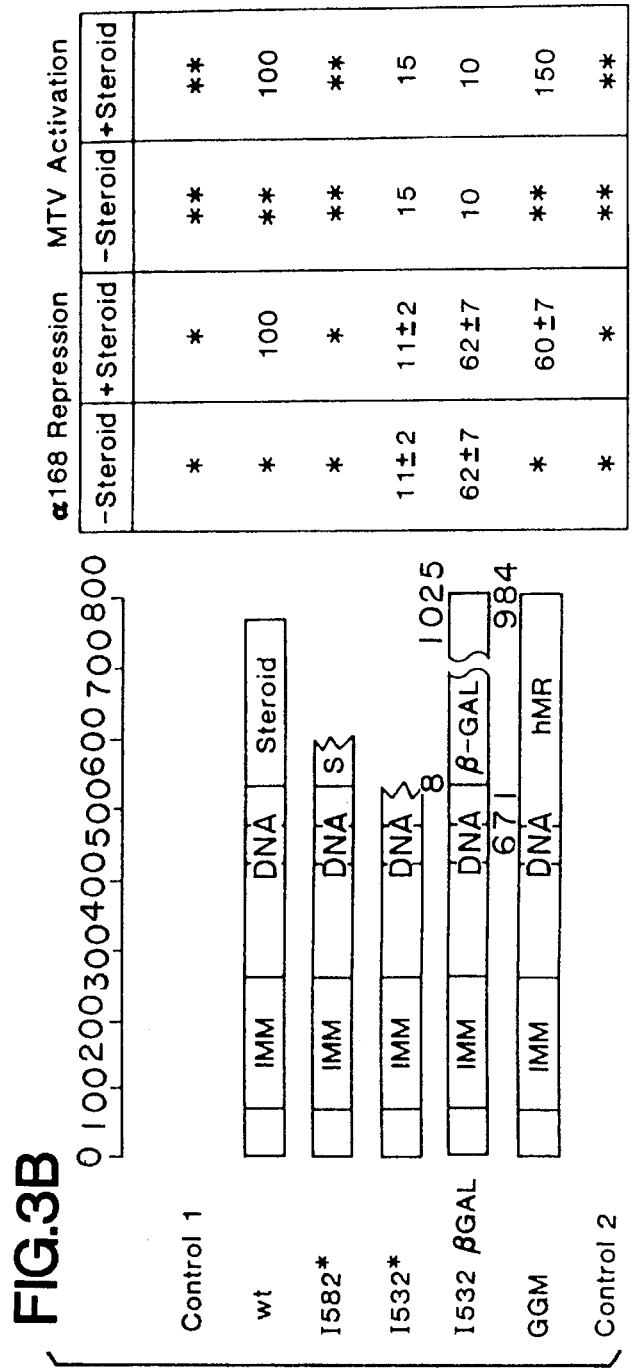

FIGS. 3A and 3B shows the relative CAT-activity of wild-type hGR, truncated hGR's and several hGR fusion proteins. hGR fusion proteins are assayed as described above. For I582*, wild-type hGR (hgrwt), I532* and the I532*-β-galactosidase fusion, the hormone used is dexamethasone; for the fusion protein GGM, the hormone used is aldosterone.

In FIG. 3B, the general make-up of the various hGR-derived proteins is illustrated. Thus, I582* is a truncated hGR having only 582 amino acids; I532* is a truncated hGR having only 532 amino acids; I532*-β-galactosidase is a fusion protein comprising amino acids I-532 from hGR, plus amino acids 8–1025 from β-galactosidase, made by inserting the 3030 bp BamHI LacZ fragment of pBG-1, a derivative of pSK105, in frame into the BamHI site of I532 (Casadaban et al., *Methods in Enzymology* Vol 100, 293, Academic Press (1983)); and GGM is a fusion protein constructed by first introducing an additional XhoI site into both the hGR at nucleotide position I596 (Hollenberg et al., *Nature* 318, 635 (1985)) and the human mineralocorticoid receptor (hMR) at nucleotide position 2233 (Arriza et al., *Science* 237, 268 (1987)) and then inserting the appropriate XhoI fragment of the hMR into the hGR. This gave a receptor with amino acids 1–489 of hGR and 671–984 of hMR.

FIG. 3B compares the repression activity of the carboxy terminal fusion proteins on the alpha168 promoter to activation on the mouse mammary tumor virus (MTV) promoter. The percentage of wild type activity is calculated by assigning RSV control plasmid as zero activity and the wild type hGR as 100 percent in each experiment, plus or minus the standard error of the mean. Control 1 and control 2 refer to transfection with RSV control plasmid. Control 1 plus the next 4 constructions used dexamethasone as the steroid, while control 2 and GGM used aldosterone as the steroid. The numbers on the I532*-β-galactosidase construct refer to β-galactosidase amino acid numbering from Casadaban et al., *Meth. Enzymol.*, Vol. 100, pp. 298–308 (1983), and the numbers on GGM refer to hMR amino acid numbering from Arriza et al., supra (1987). An "*" indicates that activity is less than 10 percent wild type repression activity, "**" indicates that activity is less than 1 percent wild type activation activity.

Novel sequence specific repressors can be created by attaching heterologous protein sequences to the carboxyl terminal side of the hGR DNA binding domain. In one case, *E. coli* β-galactosidase (β-gal) can be fused in frame to the carboxyl terminal side of the hGR DNA-binding domain and assayed for regulatory properties. On the mouse mammary tumor virus (MTV) promoter, this hybrid functions as a constitutive activator with properties unchanged from that of the parental truncated receptor. On the alpha168 promoter, the fusion protein is a constitutive repressor whose activity is dramatically increased when compared to the truncated receptor, I532*. Thus, the addition of a heterologous *E. coli* protein sequence to the DNA binding domain of the hGR is sufficient for generation of a functional transcriptional repressor.

The results of this study provide several means to distinguish positive and negative regulatory effects of the hGR. First, the amino terminal domain that contains a potent activator sequence, $T_1$, is not necessary for trans-repression. Indeed, it has been found that deletion of $T_1$ engenders a more potent repressor. This argues that even when functioning as a repressor, the amino terminal region of the hGR retains some residual positive activity.

The fact that certain modifications of the hGR produce a receptor that retains normal repressor function but has lost virtually all positive activation capability demonstrates that the process of activation can be mechanistically distinguished from that of repression. This observation further indicates that the function of the DNA-binding domain is more than simply to locate an appropriate regulatory sequence. Moreover, the result also implies that activation requires an additional event subsequent to DNA-binding that is apparently not critical for negative control.

Yet another distinction between activation and repression is that a β-galactosidase moiety functionally replaces the hGR carboxyl terminus only in repression. Removal of the carboxyl terminus results in a receptor variant with minimal repression activity.

EXAMPLE 4

Thyroid Receptor Mediated Negative Regulation

Thyroid receptor (TR) differs from the glucocorticoid receptor (GR) in that the TR is able to bind to its cognate response element even in the absence of its associated ligand. In view of these differences, it is of interest to determine if modifications to the TR analogous to the modifications investigated for the GR will provide similar trans-repressing derivatives.

The vectors employed for these studies are prepared as follows:

Expression vector RS-rTRα is constructed as described by Thompson et al, Proc. of the Natl. Acad. of Sci., Vol. 86, pp. 3494–3498 (1989).

The expression plasmid RS-v-erbA is generated by excising the coding sequence of the cloned gag-v-erbA gene [Vennström et al., J. Virol. Vol. 36, pp. 575–585 (1980)], followed by appropriate modification of the 5' and 3' ends and insertion between the Kpn1 and BamH1 sites of the vector pRS-hGR$_{NX}$ [Giguere et al., *Nature* 330, 624 (1987)]. Synthetic oligonucleotides encoding a palindromic response element [TRE$_p$; TCAGGTCATGACCTGA; see Glass et al., Cell Vol. 54, pp. 313–323 (1988)] flanked by HindIII adaptor sequences are inserted into the unique HindIII cloning site in pBL-CAT2 [Luckow et al., *Nuc. Acids Res.* 15, 5490 (1987)]. Plasmids containing one or multiple copies of the TRE are identified by restriction enzyme mapping and sequence analysis. Hybrid genes are constructed using restriction sites common to both rTRα [Thompson et al., Science, Vol. 237, pp. 1610–1614 (1987)] and v-erbA genes [Damm et al., EMBO J. Vol. 6, 375 (1987) and Vennström et al., *J. Virol.* 36, 575 (1980). A schematic organization of the rTRα and v-erbA protein sequences is given in FIG. 3A. cDNAs encoding these proteins are cloned into an RSV expression vector. The "DNA" and "$T_3/T_4$"designations in the Figure refer to the DNA- and thyroid hormone binding domain, respectively. The 12 amino-terminal amino acids of chicken c-erbA/TRα are replaced by part of the retroviral gag-gene, resulting in the synthesis of a P75$_{gag-v-erbA}$ hybrid protein. In addition, v-erbA differs from chicken c-erbA/TRα in 2 amino acids in the DNA binding domain and 9 amino acids plus a 9 amino acid deletion in the-hormone binding domain. The comparison to rat TRα shown in FIG. 3A reveals an additional 17 amino acid differences that are species specific and also found in comparison between chicken and rat TRα deduced amino acid sequences. The numbers on top of the constructs shown in FIG. 3A indicate amino acid positions.

TR(Δ154/317) is created by deleting the Pst1 fragment in the ligand binding domain of rTRα. Replacement of the rTRα carboxy-terminus by a Pst1-Xba1 fragment from a v-erbA-neo construct [Sap et al., *Nature* 324, 635 (1986)] generates TR(a154/317)erbA. The plasmids TR(317)erbA, TR(154erbA and TR(154/317) are generated by reinserting the Pst1 fragments from either rTRα or v-erbA into the unique Pst1 site of either plasmid. All modifications are performed on a subcloned fragment from the ligand binding domain of rTRα and hybrid expression constructs are generated by replacing the Xba fragment of RS-rTRα with the corresponding chimeric fragments.

COS cells are grown in DMEM with 5% T3 free bovine serum and transfected using DEAE dextran [Giguere et al., *Cell* 46, 645 (1986)]. After 36 hours, cells are harvested and extracts prepared as described by Kumar et al., in Cell, Vol. 55, 145 (1988), except that the buffer was 20 mM Hepes (pH 7.8), 0.4M KCl, 2 mM dithiothreitol (DTT) and 20% glycerol. DNA binding reactions and gel electrophoresis are performed essentially as described by Glass, et al., in Cell, Vol. 54, 313 (1988). Aliquots containing 6–10 μg of total protein are diluted so that the final concentration of KCl is 80 mM, then incubated with 2 μg of polydeoxycytidylic acid (poly[dC]) for 20 min at room temperature. At this time, 25–50 fmoles of a $^{32}$P-labeled oligonucleotide encoding the palindromic TRE was added. The reaction mixture was incubated at 22° C. for 30 min and then loaded on a 5% polyacrylamide gel containing 50 mM Hepes pH 7.8. Competitor DNAs were added prior to the addition of the labeled oligonucleotide.

The DNA binding mutant i95TR was constructed by partial digestion of rTRα with PvuII and adding a BamHI linker (12 mer) to restore the open reading frame. The position of the linker was verified by restriction enzyme mapping and sequence analysis.

The DNA binding mutant i95(154)erbA was constructed by partial digestion of TR(154)erbA with PvuII and adding a BamHI linker (12 mer) to restore the open reading frame. The position of the linker was verified by restriction enzyme mapping and sequence analysis.

Figure 4A:
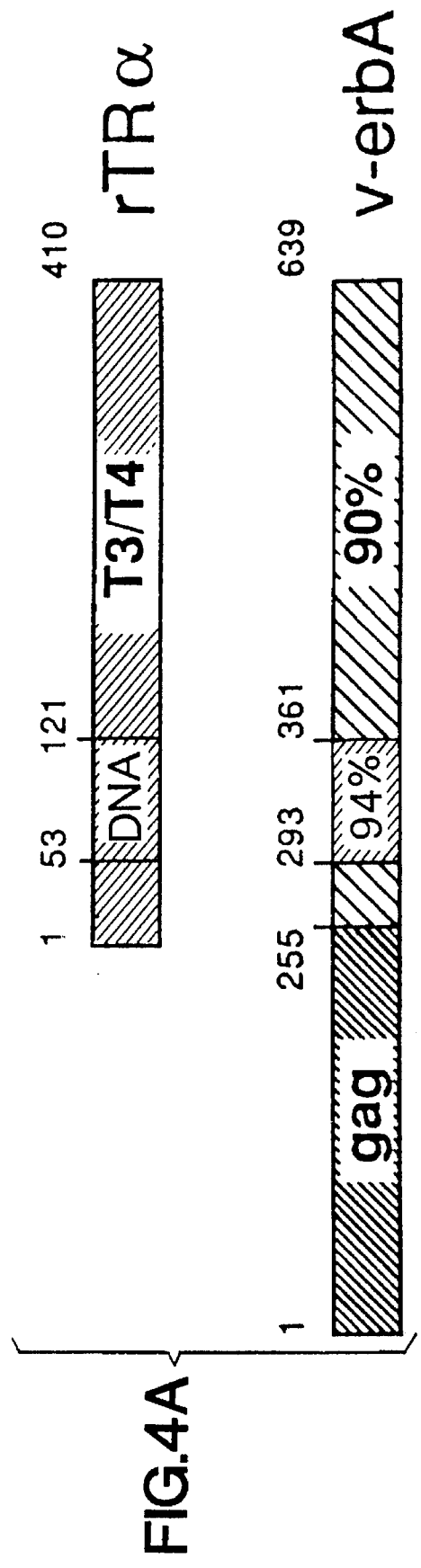
FIGS. 4A and 4B illustrate several expression and reporter constructs.
Figure 4B:
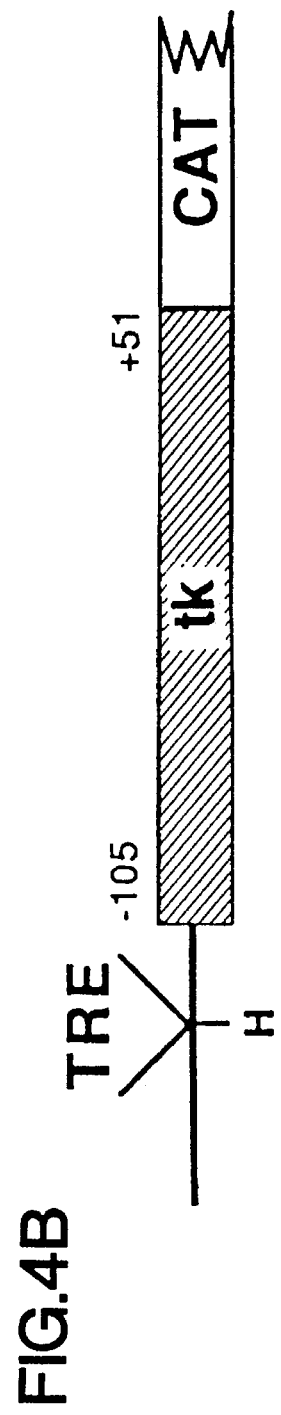

First, the transcriptional activity of both the rat thyroid hormone α receptor (rTRα) [Thompson, et al., *Science* 237, 1610 (1987)] and the v-erbA oncogene product is assessed by determining their ability to regulate expression of thyroid hormone responsive reporter genes (see FIG. 4A). The constructs shown in the Figure contain oligonucleotides corresponding to previously identified thyroid hormone response elements [Glass et al., *Nature* 329, 738 (1987) and Glass et al., *Cell* 54, 313(1988) ] linked to a thymidine kinase-chloramphenicol acetyltransferase (tk-CAT) fusion gene [Luckow et al., *Nuc.. Acids Res.* 15, 5490 (1987)] (see FIG. 4B). The reporter gene constructs used, and shown in FIG. 4B, contain oligonucleotides encoding the respective $T_3$ response elements (TRE) inserted into the HindIII site (H) upstream of the tk promoter-CAT construct. Expression plasmids encoding rTRα or v-erbA under the transcriptional control of the RSV long terminal repeat are cotransfected with one of the reporter plasmids into CV1 cells, which lack significant levels of endogenous TR.

CV-1 cells are co-transfected with the reporter construct tk-CAT, tk-TRE$_p$-CAT or tk-TRE-$_{GH3}$-CAT; the respective expression plasmid (RS-rTRα or RS-v-erbA) and the internal reference plasmid RSV-βGAL. In the control experiments, a construct carrying the rTRα coding sequences in reverse orientation (RS-3'-5') is used.

Transfection of tk-TRE$_p$-CAT or the parental vector tk-CAT results in a high basal level of CAT activity that is only marginally stimulated by the addition of thyroid hormone. In contrast, cotransfection with the TR expression vector RSV-rTRα results in marked effects on tk-TRE$_p$-CAT expression. In the absence of thyroid hormone, there-is observed an 80% decrease in basal CAT activity (referred to as "low basal level activity"), indicating that TR expression provokes a ligand-independent inhibitory effect on transcription. Addition of a thyroid hormone, triiodothyronine [$T_3$], to a final concentration of 100 nM results in a 20 fold stimulation of tk-TRE$_p$-CAT. This corresponds to a 3–5 fold stimulation over the basal level of activity obtained in the absence of TR expression.

The regulatory function of the rTRα is not restricted to the TRE$_p$; the TRE from the rat growth hormone gene is also able to sustain hormone-independent and dependent transcriptional responses. This functional assay enables a direct determination of the putative transcriptional activity of the v-erbA oncogene product. Since v-erbA has lost its ability to bind thyroid hormone but retains an intact DNA binding domain, it is reasonable to expect that it would function as a constitutively active TR. Unexpectedly, cotransfection of v-erbA with either reporter plasmid does not stimulate the transcription, but rather resembles the negative regulatory effects of rTRα in the absence of hormone. Thus, in cells expressing v-erbA, CAT activity is reduced by 80% from the high basal level, and can not be relieved by the addition of $T_3$.

Figure 5A:
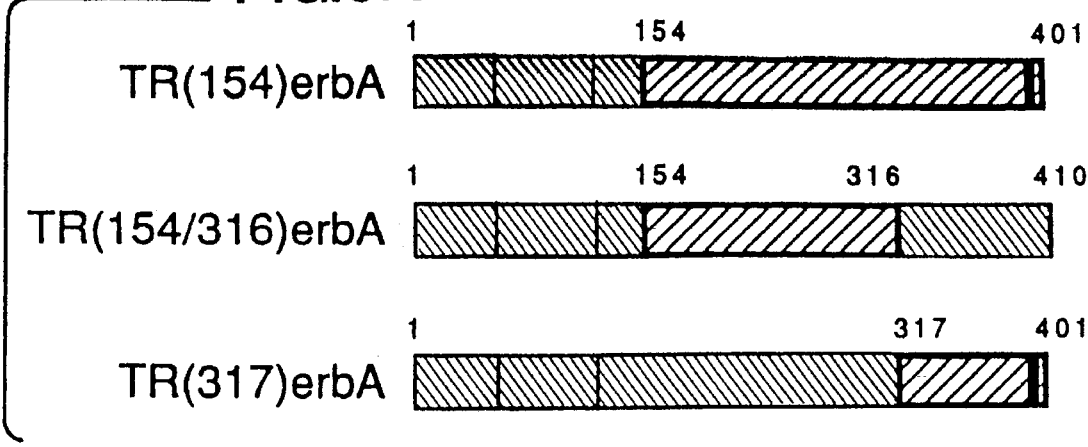
FIGS. 5A and 5B show the structure and activity of rat TRα/v-erbA chimeric proteins.
Figure 5B:
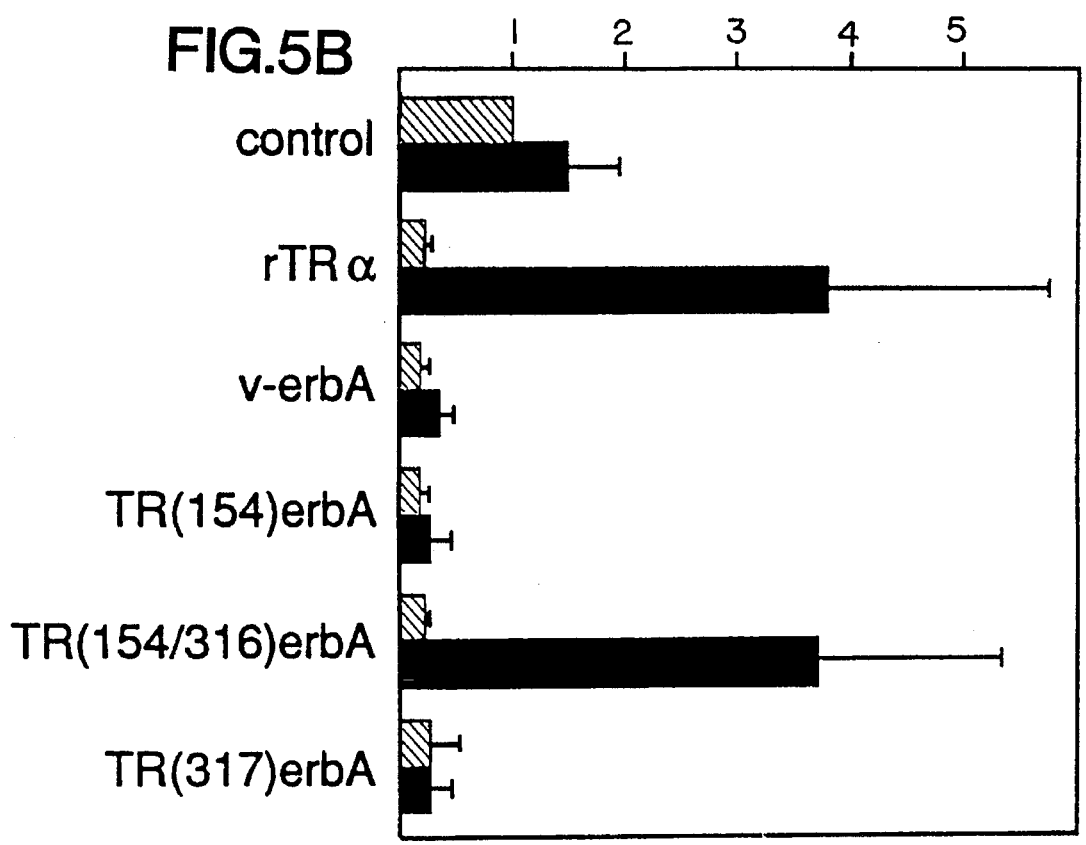

To identify the effect of different mutations in v-erbA on the altered properties of this protein (relative to its progenitor, TR), and to further dissect the processes of activation and repression, chimeric receptors of the v-erbA oncogene [see Damm et al., *EMBO J.* Vol. 6, pp. 375–382 (1987) and Vennström et al. *J. Virol.* Vol. 36, pp. 575–585 (1980)], and the rat TRα [Thompson et al., (1987), supra] are constructed. A schematic representation of the structure of the rat TRα/v-erbA chimeric proteins is presented in FIG. 5A. Numbers on top of each construct indicate amino acid positions. The black bar indicates the deletion of 9 amino acids in v-erbA, resulting in fusion proteins of 401 amino acids compared to the 410 amino acid of the protein with intact carboxy-terminus. In FIG. 5B, positive and negative regulation of CAT activity from tk-TRE$_p$-CAT is shown, using the indicated expression vectors. The histogram summarizes the average values of 2–6 independent transfection experiments. Stippled bars in the histogram indicate the presence of no hormone; while striped bars in the histogram indicate the presence of 100 nM $T_3$.

From amino acids 154 to 410, v-erbA differs from rTRα in 26 amino acids and a deletion of 9 amino acids close to the carboxy-terminus. Swapping this region of rTRα with v-erbA gives rise to the hybrid TR(154)erbA (FIG. 5A), whose properties are virtually identical to the v-erbA homologue (FIG. 5B). Thus, the mutations in the DNA binding domain and flanking amino acids are not crucial to the v-erbA phenotype.

Substitution of an internal region of rTRα ligand binding domain (at amino acids 154–316), creates a $T_3$ responsive hybrid (TR(154/316)erbA) that functions like the natural receptor. In contrast, replacement of the carboxy-terminal 93 amino acids of rTRα with the corresponding sequence of v-erbA, containing the 9-amino-acid deletion and additional 11 amino acid differences, yields the hybrid protein TR(317)erbA with suppressor properties identical to the viral oncogene product.

Figure 6A:
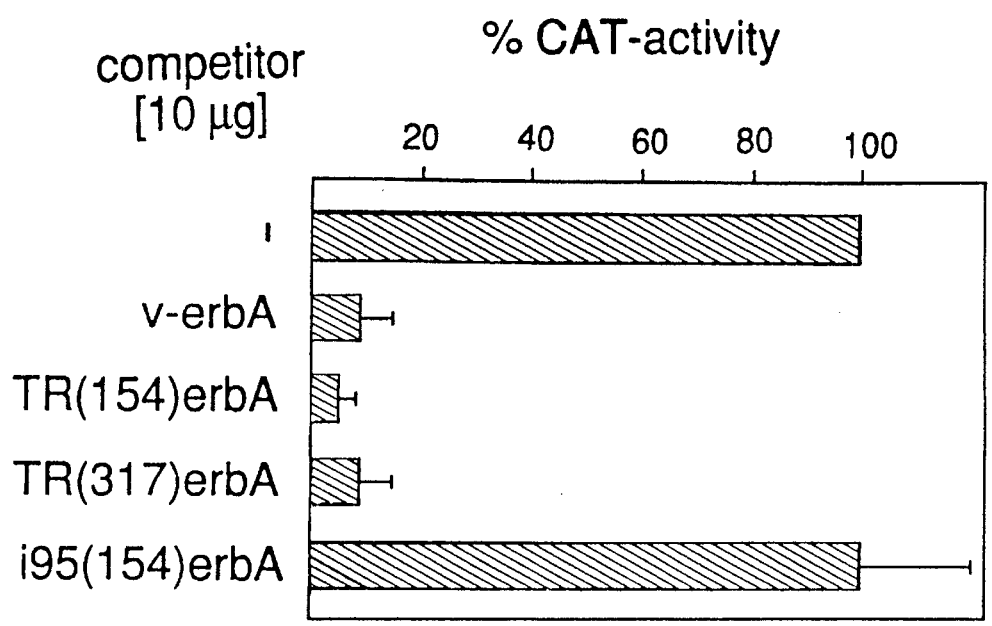
FIGS. 6A and 6B show a comparison of $T_3$ induction of CAT activity by thyroid receptor, v-erbA, and hybrid Tr/v-erbA receptors.
Figure 6B:
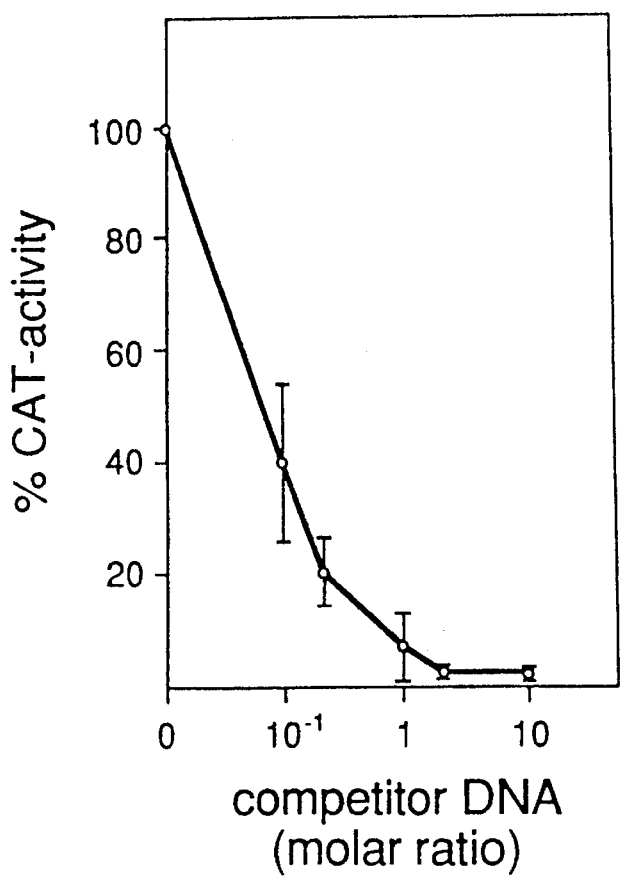

To examine the effect of v-erbA on the function of endogenous thyroid receptor, cotransfection studies in CV1 cells are performed. The reporter gene tk-TRE$_p$-CAT (0.5 µg) is cotransfected into CV-1 cells with 1 µg of rTRα expression vector and the internal control plasmid RSV-β-GAL. In addition, a 10-fold excess (10 µg) of the expression plasmids indicated in FIGS. 6A and 6B is cotransfected with rTRα. In the run designated by (-), 10 µg of the control plasmid, RS-3'-5', is used. The average values of 2–6 independent transfection experiments are shown in the histogram in FIGS. 6A and 6B. All experiments are performed in the presence of 100 nM $T_3$.

As shown in FIG. 6A, a 10-fold molar excess of v-erbA reduces by 90% the thyroid hormone dependent induction of the reporter gene transcription by rTRα. The hybrid constructs TR(154)erbA and TR(317)erbA also exhibit v-erbA-like activities, provoking a virtually complete repression of the $T_3$ and rTRα induced stimulation of the reporter gene. The activity is, however, dependent on the presence of an intact DNA-binding region since the DNA-binding domain mutant i95(154)erbA, fails to compete.

Similarly, $T_3$ induction is blocked by v-erbA and the chimeric constructs when the TRE$_p$ is placed in the context of the MTV promoter. One prediction of these results is that an inverse relationship exists between the activity of the TR and the concentration of the competitor product. To examine this prediction, varying molar ratios of TR(154)erbA and the rTRα expression vector were cotransfected and hormone responsiveness was assessed. Thus, the reporter gene tk-TRE$_p$-CAT (0.5 μg) was cotransfected into CV1 cells with 1 μg of expression vector RS-rTRα and increasing quantities of the non-hormone binding competitor TR(154)erbA. The amounts of RSV-promoter was held constant in all transfections by the addition of the control plasmid, RS-3'-5'. Shown are the average values of three independent transfection experiments. Cells were grown in the presence of 100 nM T$_3$.

As one might expect, increasing quantities of TR(154)erbA lead to decreasing activity of the rTRα (see FIG. 6B). In this assay, even small amounts of TR(154)erbA are potent, with a 3:1 plasmid ratio completely blunting the hormone induced response.

Although it is generally assumed that the ability of a hormone receptor to bind DNA is ligand dependent [Evans, *Science* 240, 889 (1988)], the results presented herein, as well as previous observations [Lavin et al., *J. Biol. Chem.* 263, 9418 (1988)] challenge this convention. The down-regulation of transcription from the responsive promoter is presumably a consequence of the ability of the receptor to recognize and bond to its cognate response element in the absence of hormone. Two pieces of evidence support this proposal. First, an intact DNA binding domain is necessary for both the gel retardation experiments and the observed transcriptional effects. Second, in the absence of the response element no significant repression is observed, whereas a tandem copy of the TRE potentiates both positive and negative transcriptional effects. Although positive synergism has been observed by glucocorticoid and estrogen receptors and their respective response elements [Schüle et al., *Science* 242, 1418 (1988) and Strähle et al., *EMBO J.* 7 3389 (1988)] the negative synergism observed here is without apparent precedent.

EXAMPLE 5

Retinoic Acid Receptor Mediated Negative Regulation

Figure 7:
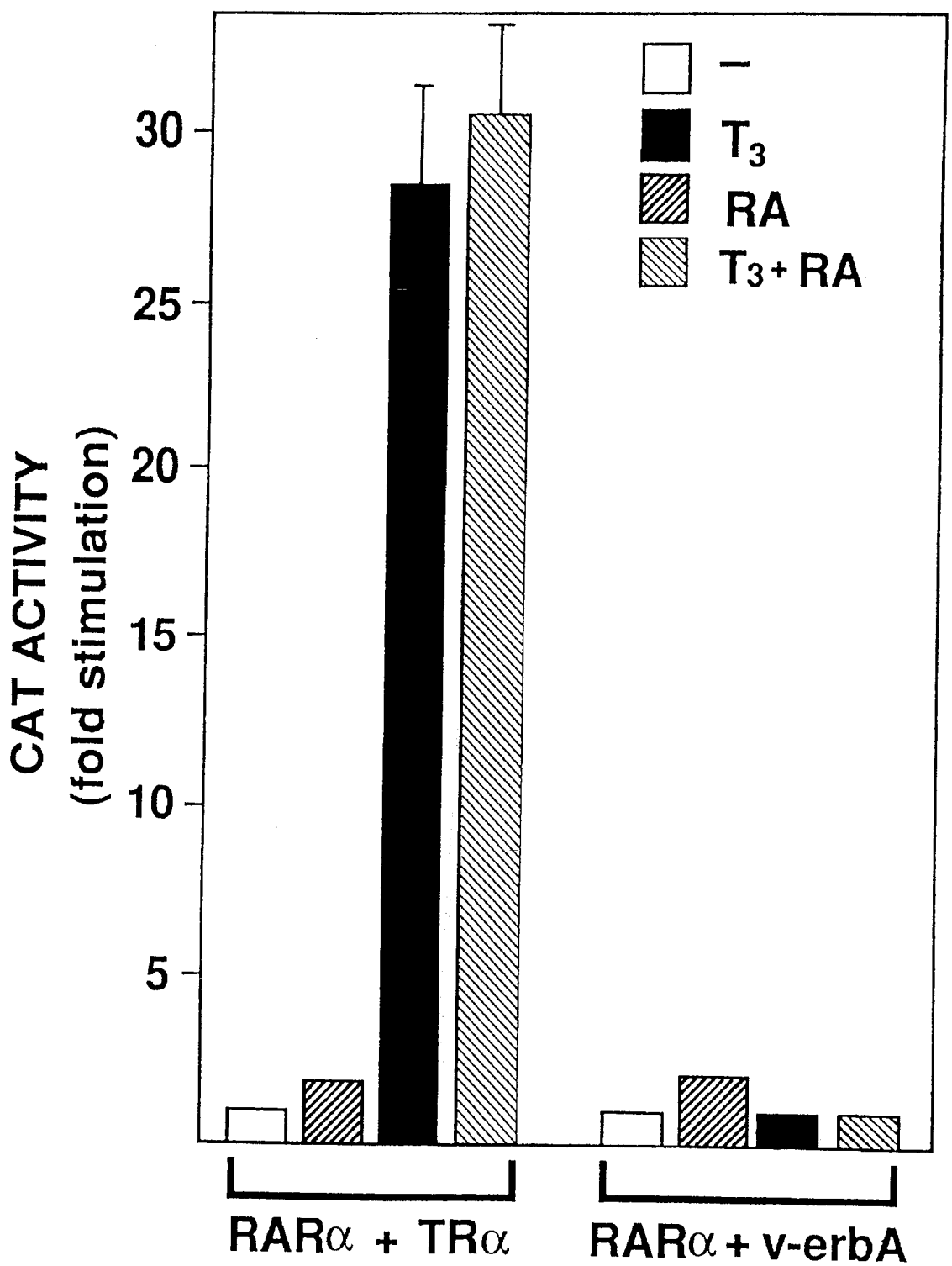
FIG. 7 shows the competition of TRα or v-erbA with RA induced transcriptional activation by RARα.

To investigate the possible positive and/or negative interaction of RARα with TRα and v-erbA, CV-1 cells are cotransfected with the RARα and reporter plasmid in the presence of TRα or v-erbA (FIG. 7). In the Figure, TRα or v-erbA compete with the RA induced transcriptional activation by RARα. RARα expression vector (1.0 μg) is cotransfected with reporter plasmid ΔMTV-TRE$_p$-CAT (1.0 μg) along with TRα (5.0 μg) or with v-erbA (5.0 μg). Plasmids are introduced into CV-1 cells (maintained in DME medium supplemented with 5% calf bovine serum), 5×10$^5$ per 10.0 cm dish, by calcium phosphate precipitation.

The expression plasmids, RARα TRα and v-erbA are under control of the RSV promoter as previously described by Damm et al. in Nature, Vol 339, 593 (1989) and Umesono et al, in Nature, Vol 335, 262 (1988). The cells were cultured for 36 hours in Dulbecco-modified Eagle medium containing 10% resin-charcoal stripped calf bovine serum [Samuels et al, Endocrinology, Vol 105, 80 (1979)] with or without hormone as indicated and subsequently prepared for CAT activity through three cycles of freeze thawing as described by Gorman et al, Mol. Cell. Biol., Vol 2, 1044 (1982). An aliquot of the cell extracts was normalized by β-gal activity prior to carrying out the CAT assay. The hormone is added at a final concentration of 100 nM. These data are the average of 4 independent experiments.

A 5 fold molar excess of TRα reduces the RA dependent induction in CAT activity by 90%. No inhibition of transcription is observed when both T3 and RA are added simultaneously. Therefore, in the absence of T3, the TRα prevents the RA induced activation of gene expression by the RARα, whereas in the presence of T3, one observes activation, presumably through the TRα. Similar observations for the TR inhibition of RAR activation have recently been observed by Graupner et al., Nature, Vol 340, 653 (1989) and Brent et al., The New Biologist, Vol 1, 329 (1989). A similar competition of the RA induced gene activation is observed when v-erbA is cotransfected along with the RARα.

Figure 8:
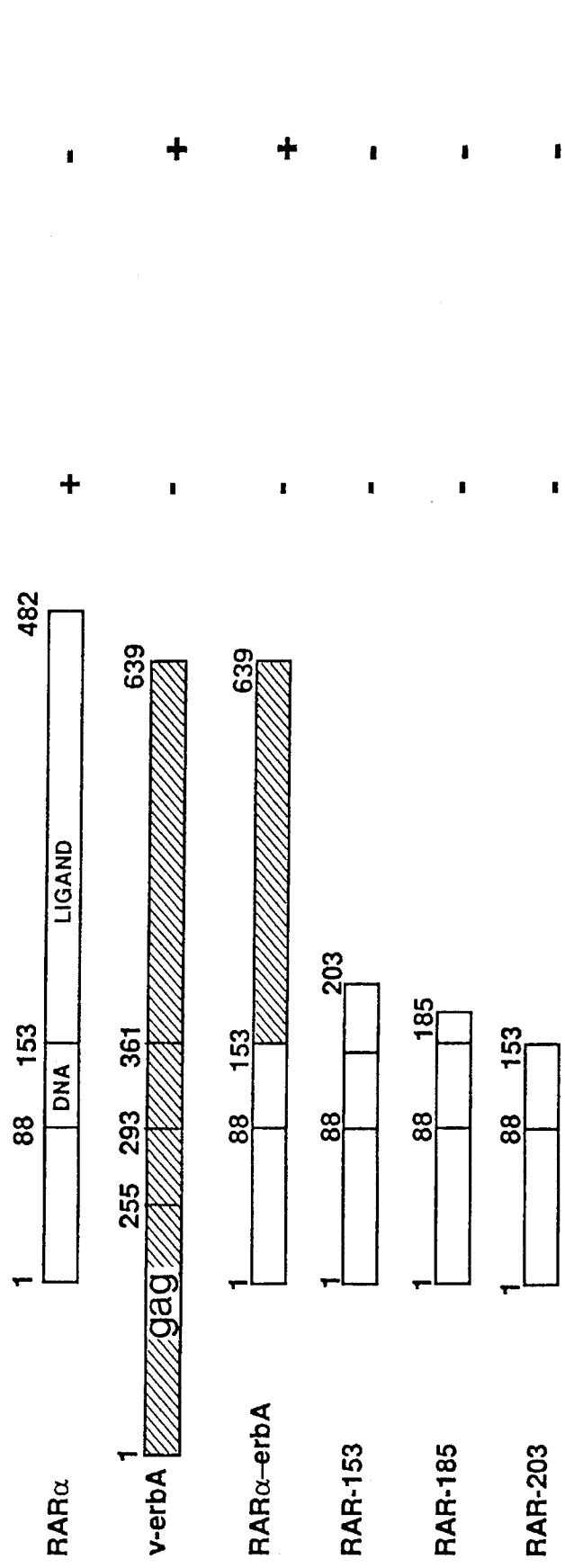
FIG. 8 summarizes the structure and activity properties of several RAR hybrids and mutants.

To investigate whether one could confer a dominant negative effect directly onto the RARα, mutant RARαs are created consisting of a series of RAR truncations as well as a hybrid RARα-erbA fusion. Since the RAR functions as a ligand dependent transcription factor, a mutant that contains an alteration or deletion in the ligand binding domain but with an intact DNA binding domain may confer a dominant negative phenotype. In fact, the results set forth in Example 4 above demonstrate that replacing the ligand binding domain, located in the carboxyl terminus of the TRα, with the carboxyl terminus of v-erbA results in a hybrid TRα-erbA molecule that functions as a dominant negative mutant of the TRα. Therefore, a similar fusion between RARα and v-erbA was constructed by replacing the ligand binding domain of the RARα, located in the carboxyl terminal, with the carboxyl terminus of v-erbA (FIG. 8). The hybrid RARα-erbA fusion was constructed by removing the N-terminus and DNA binding domain of TR317-erb-A, see Damm et al, Supra, and replacing it with the corresponding N-terminus and DNA-binding domain the RARα (thus creating a RARα-erbA hybrid protein). Truncation mutants give the last amino acid of RARα before the insertion of a translation stop signal at the indicated position. The RAR 185 and 203 truncation mutants were constructed by using unique restriction sites present in the wild type receptor whereas RAR 153 was constructed by inserting a stop codon at position 153 RARα following creation of a unique Xho site at this position. Retinoic acid was added at a final concentration of 100 nM.

In the transactivation experiments, a positive response corresponds to a 25 fold increase in CAT activity upon retinoic acid addition. A negative response corresponds to no transactivation upon retinoic acid addition. In the competition experiments, a positive response corresponds to greater than an 80% antagonism of the retinoic acid induced transactivation, while a negative response corresponds to no competition upon retinoic acid addition.

Figure 9:
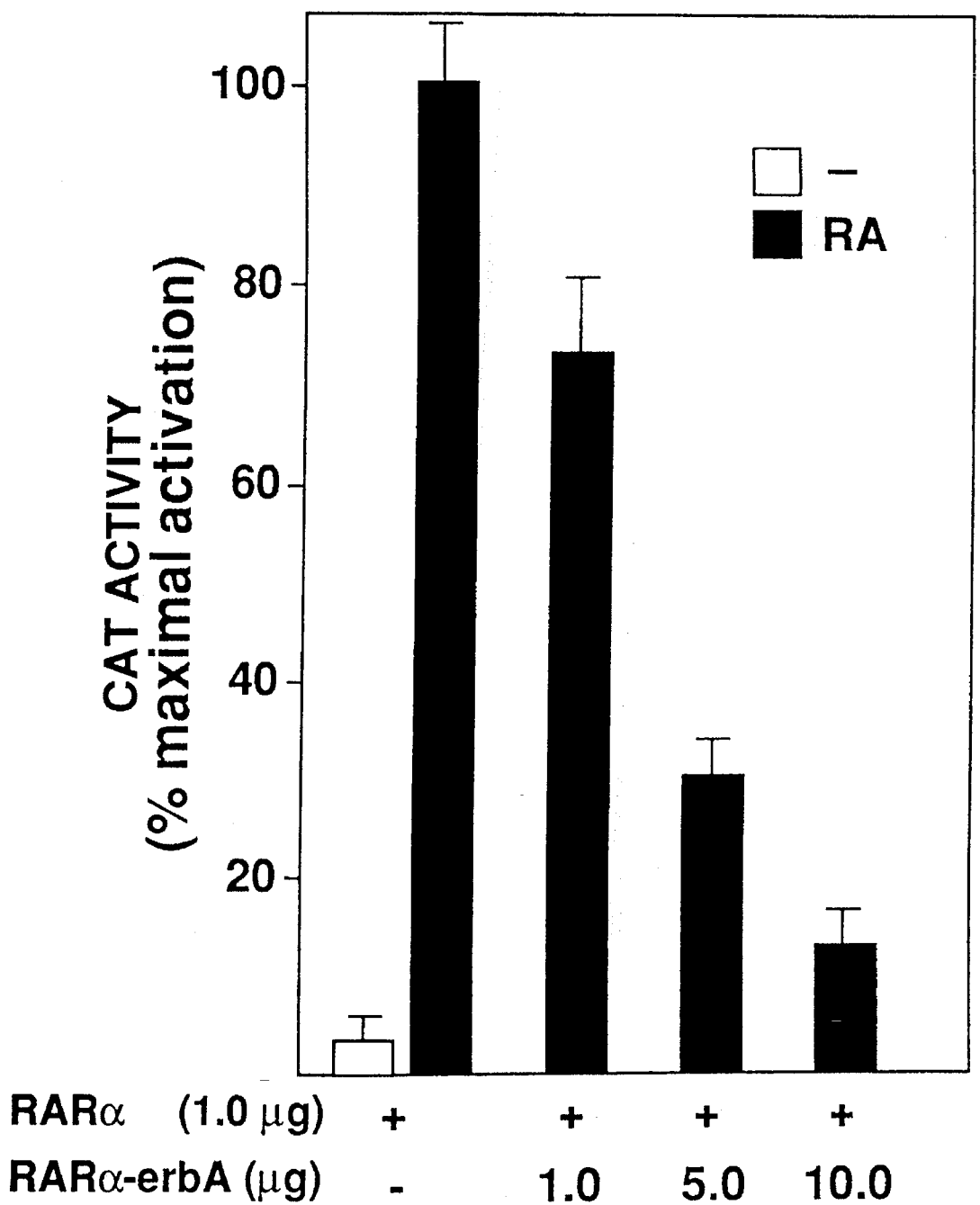
FIG. 9 shows the competition of RA induction by RARα-v erbA fusion protein.

The RARα-erbA protein does not act by itself as a transcriptional activator whether hormone is present or absent. However, when the RARα-erbA fusion is cotransfected with the RARα, it functions as a RARα antagonist. See FIG. 9.

CV-1 cells are cotransfected with RAR expression vector (1.0 μg), ΔMTV-TRE$_p$-CAT reporter plasmid (see Umesono et al, Supra) (5.0 μg), reference plasmid (5.0 mg), along with increasing amounts of RARα-erbA and carrier plasmid up to 20.0 mg. The addition of RSV-promoter is held constant in all transfections with the addition of the carrier plasmid. The % maximal response refers to CAT induction observed with the RAR wild type receptor in the presence of 100 nM RA.

This activation corresponds to a RA induction of 25 fold. All data are the average of 4 independent experiments.

RARα-erbA is also capable of antagonizing the RA induced activation of the RARβ and RARγ. Therefore, replacement of the carboxyl terminus of RARα with the carboxyl terminus of v-erbA confers a dominant negative phenotype onto the RARα. In contrast, RAR-mutants consisting of a series of carboxyl terminal truncations do not act as transcriptional activators when transfected by themselves nor do they function as RARα competitors when transfected in conjunction with the RARα. These data on the RAR truncations are in part at odds with the recent observation of Espeseth et al., Genes and Dev., Vol. 3, 1647 (1989), who reported that an RARα mutant, virtually identical to RAR-185, gave rise to a small percentage of stable F9 clones that did not differentiate in response to RA and therefore, hypothesized that this RAR truncation mutant functioned as a dominant negative RAR.

Figure 10:
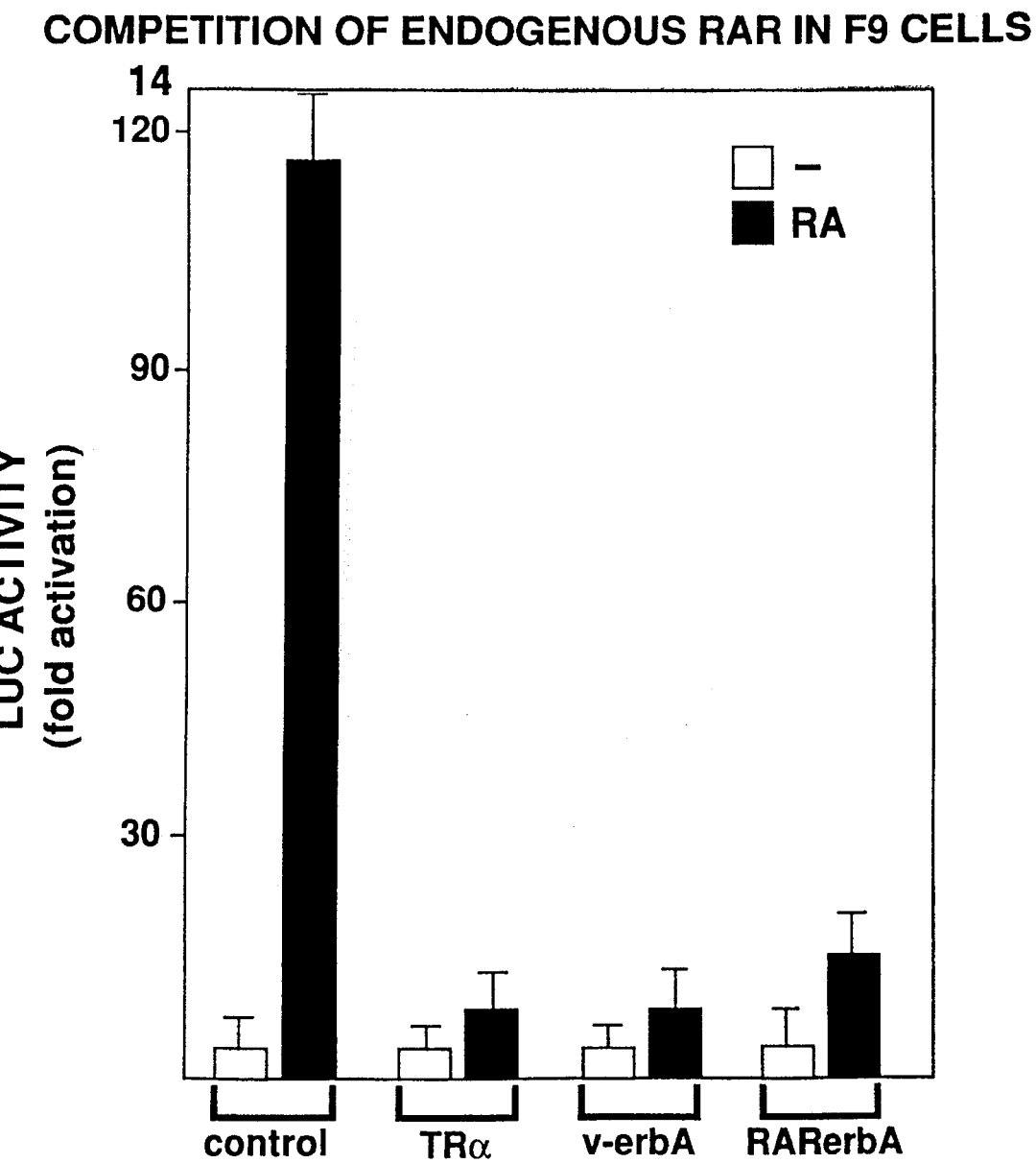
FIG. 10 shows the competition of RA induced transactivation of endogenous RARs in F9 tetracarcinoma stem cells.

The properties of the RARα-erbA fusion along with the v-erbA and TRα, are further investigated by examining their ability to repress/antagonize an endogenous RAR(s). F9 cells have been established as a cellular model for RA dependent differentiation. They contain receptors for the α,β, and γ subtypes of the RAR family; RARα and RARγ are present in undifferentiated stem cell whereas RARβ is induced upon RA treatment. See, for example, Strickland and Mahdavi, in Cell, Vol 15, 393 (1978); Sporn et al, in *The Retinoids*, Vol 1-2, Academic Press (Orlando, Fla., 1984); and Hu and Gudas in Mol. Cell. Biol., Vol 10, 391 (1990). Transfection of either RARα-erbA, TRα or v-erbA into F9 cells results in a strong inhibition of the RA induced transactivation (FIG. 10). F9 cells (maintained in DMEM supplemented with 10% CBS) are transfected by the calcium phosphate method with the reporter ΔMTV-TRE$_p$-Luc (5.0 μg), 5.0 mg of either the control plasmid (RSV-CAT), or RSV-TRα, RSV-verbA or RSV RARα-erbA. 5.0 μg of reference plasmid and 5.0 μg of carrier plasmid. Cells are cultured for 24 hours in the presence or absence of 100 nM RA as indicated. The reporter construct is exactly the same as ΔMTV-TRE$_p$-CAT except that the gene encoding firefly luciferase [see DeWet et al., Mol. Cell. Biol., Vol 7, 725 (1987)] has been substituted for CAT in the reporter plasmid. Cells were cultured for 24 hours following the addition of the hormone and subsequently harvested and assayed for luciferase as described by Hollenberg et al, in Cell, Vol 55, 899 (1988). Data are the average of 4 independent measurements.

EXAMPLE 6

Glucocorticoid Receptor-v erbA and GR-βGal Fusion Proteins

The above observations that the RARα-erbA fusion protein functions as a dominant negative RAR, in conjunction with the ability of TRα-erbA hybrid to function as a TRα inhibitor, suggests that steroid-erbA hybrid receptors may provide a general approach for creating specific hormone receptor antagonists. Therefore, a fusion between GR and erbA was created (GR-erbA, FIG. 11) by substituting the carboxyl terminus of v-erbA for the ligand binding domain of the GR.

In the Figure, wild type GR is shown at top with numbers indicating amino acid positions. The DNA and ligand binding domains are also indicated. The hybrid GR-erbA fusion is constructed by removing the ligand binding domain of the GR and replacing it with the carboxyl terminus of v-erbA, similar to the RAR-erbA fusion protein described above. The three truncation mutants give the last amino acid before the carboxyl terminal nonsense peptides. For GR-532βgal, *E. coli* βgal was fused in frame to position 532 of the GR as described by Oro et al. in Cell, Vol 55, 1109 (1988). It encodes a protein that expresses β-galactosidase as well as the glucocorticoid receptor properties reported by Oro et al, Supra.

For the transactivation experiments, CV-1 cells are cotransfected with expression vector (1.0 μg), the reporter, MTV-Luc (5.0 μg), RSV-CAT (5.0 μg) as the internal control and carrier plasmid up to a total of 20.0 μg. Data is reported as % maximal response and refers to luciferase induction observed with the GR wild type in the presence of the synthetic glucocorticoid, dexamethasone at $1 \times 10^{-7}$M. This activation corresponds to an induction of 3000 fold.

Figure 11:
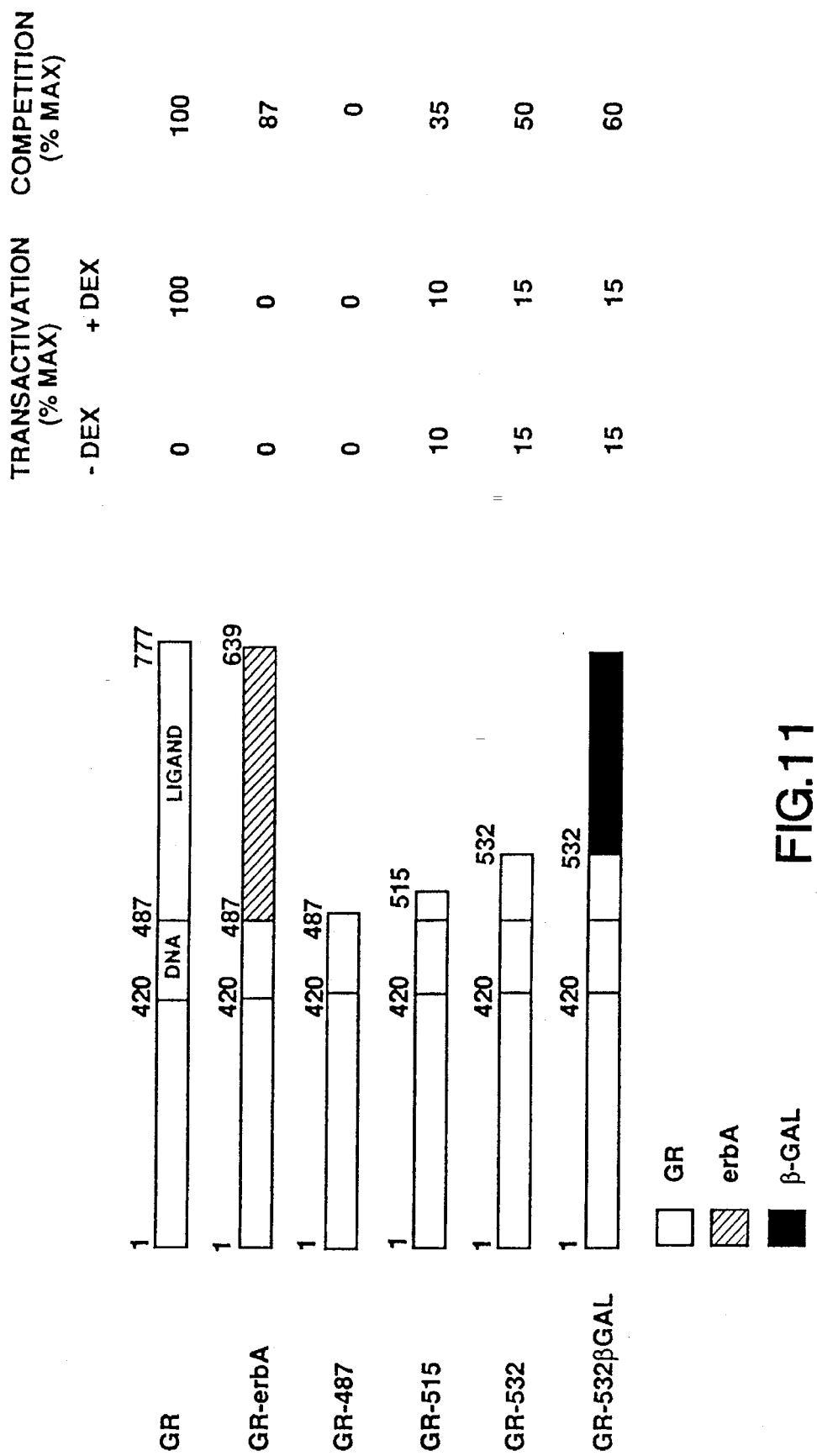
FIG. 11 summarizes the structure and activity of several GR hybrids and mutants.

For the competition experiments, CV-1 cells are cotransfected with 1.0 μg of the GR expression vector, 5.0 μg of MTV reporter, 5.0 μg of competitor along with 5.0 μg of RSV-CAT as the internal control and carrier plasmid up to a total of 20.0 μg. Dexamethasone was added at a final concentration of $1 \times 10^{-7}$M. The response refers to a % antagonism of luciferase activity With the wild type receptor in the presence of a nonspecific competitor being equal to 0%. All data in FIG. 11 are the average of four independent experiments.

The fusion protein does not activate a glucocorticoid responsive reporter gene when glucocorticoids are present or absent. However, when GR-erbA is cotransfected with GR, it functions as a GR antagonist; a 5-fold molar excess of GR-erbA reduces by 87% the dexamethasone induction of a reporter gene.

For comparison, the properties are examined of a series of GR truncation mutants to act as dominant negative competitors as well as transcriptional activators. Truncations in the carboxyl terminus result in a mutant receptor that either does not activate transcription (GR487), or result in mutants that are constitutively active receptors (GR515, GR532). When the GR truncations are cotransfected along with the wild type GR they have either no inhibitory effect or at best a slight suppressive effect upon dexamethasone induced transactivation.

To examine whether the properties exerted by placing the carboxyl terminus of GR could be substituted by another polypeptide, β-Gal was fused in frame to the carboxyl terminus of the GR at position 532. This GR-532βGal fusion protein has previously been shown to function as a negative regulator of GR transcription (See Example 3). However, this β-Gal fusion protein is constitutively active similar to the parental truncation and it reduces the GR activation by only 60%. Therefore, the ability and usefulness of the GR truncations and β-Gal fusions to act as dominant negative repressors is diminished primarily by their constitutive activity as well as their weak ability to act as GR competitors. In contrast, GR-erbA is the only mutant receptor that contains no transcriptional activity in the absence of ligand and functions to block the dexamethasone induced transactivation. In addition, GR-erbA is able to act as a very potent competitor against a constitutively active GR receptor, such as GR532, and further supports its potential to function as a dominant negative inhibitor.

The foregoing description details specific methods that can be employed to practice the present invention. Having detailed specific methods initially used to identify, isolate, characterize, prepare and use the receptors hereof, and a further disclosure as to specific entities, and sequences thereof, the art skilled will well enough know how to devise alternative reliable methods for arriving at the same information and for extending this information to other intraspecies and interspecies related receptors. Thus, however detailed the foregoing may appear in text, it should not be construed as limiting the overall scope hereof; rather, the ambit of the present invention is to be governed only by the lawful construction of the appended claims.

We claim:

1. A process for preparing a trans-repressing chimeric receptor of the steroid/thyroid superfamily of receptors, said process comprising
   expressing, in a recombinant host cell, transfected DNA encoding said receptor; wherein said receptor comprises:
   (1) a first amino acid sequence which is a DNA-binding domain, through which said chimeric receptor is capable of binding to a hormone response element of a wild type receptor, and
   (2) a second amino acid sequence which is positioned at the carboxy-terminal end of the DNA-binding domain, wherein said second sequence comprises at least the 84 carboxy-terminal amino acids of the carboxy-terminal portion of the v-erbA protein as defined by amino acid numbers 313–398 of FIG. 1;
   wherein said chimeric receptor represses transcription from a promoter normally trans-activated by said wild type receptor.

2. A process according to claim 1 further comprising:
   recovering and purifying said chimeric receptor.

3. A recombinant DNA encoding a dominant-negative trans-repressing chimeric receptor of the steroid/thyroid superfamily of receptors; wherein said receptor comprises:
   (1) a first amino acid sequence which is a DNA-binding domain, through which said chimeric receptor is capable of binding to a hormone response element of a wild type receptor, and
   (2) a second amino acid sequence which is positioned at the carboxy-terminal end of the DNA-binding domain, wherein said second sequence comprises at least the 84 carboxy-terminal amino acids of the carboxy-terminal portion of the v-erbA protein as defined by amino acid numbers 313–398 of FIG. 1;
   wherein said chimeric receptor represses transcription from a promoter normally transactivated by said wild type receptor.

4. An expression vector operatively harboring DNA according to claim 3.

5. A recombinant host cell transfected with an expression vector according to claim 4.

6. A cell culture comprising cells according to claim 5 and an extrinsic support medium assuring the viability of said cells.

7. A DNA according to claim 3 wherein said first amino acid sequence is the DNA-binding domain of said wild type receptor.

8. A DNA according to claim 7 wherein said wild type receptor is selected from: a retinoic acid receptor, a thyroid hormone receptor, a vitamin $D_3$ receptor, a glucocorticoid receptor, a mineralocorticoid receptor, an estrogen receptor, an estrogen-related receptor, an aldosterone receptor, an androgen receptor, or a progesterone receptor.

9. A DNA according to claim 8 wherein said DNA-binding domain is derived from: 1) a glucocorticoid receptor, 2) a thyroid hormone receptor, or 3) a retinoic acid receptor.

10. A DNA according to claim 9 wherein said DNA-binding domain is derived from a human glucocorticoid receptor.

11. A DNA according to claim 9 wherein said DNA-binding domain is derived from a thyroid hormone receptor.

12. A DNA according to claim 9 wherein said DNA-binding domain is derived from a retinoic acid receptor.

13. A DNA according to claim 3 wherein said first amino acid sequence is derived from said wild type receptor, and wherein said chimeric receptor has substantially no transcriptional activation activity in the presence or absence of ligand.

14. Method for producing a trans-repressing chimeric hormone receptor, said method comprising:
   replacing the ligand binding domain of a wild type nuclear hormone receptor with at least the 84 carboxy terminal amino acids of the verbA protein as defined by amino acid numbers 313–398 of FIG. 1.

15. Method for producing a trans-repressing chimeric hormone receptor, said method comprising:
   replacing the ligand binding domain of a wild type nuclear hormone receptor with a polypeptide which has at least 90% as many amino acids as the ligand binding domain of the carboxy-terminus of said wild type receptor; and wherein said polypeptide has less than about 60% amino acid identity relative to the carboxy-terminus of said wild type receptor over either:
   (i) the entire length of said polypeptide, if shorter than the carboxy-terminus of said wild type receptor, or
   (ii) any segment of said polypeptide having the same length as the carboxy-terminus of said wild type receptor,
   wherein said chimeric receptor represses transcription from a promoter normally transrepressed by said wild type receptor.

16. A process for preparing a trans-repressing chimeric receptor of the steroid/thyroid superfamily of receptors, said process comprising:
   expressing, in a recombinant host cell, transfected DNA encoding said receptor; wherein said receptor comprises:
   (1) a first amino acid sequence which is a DNA-binding domain, through which said chimeric receptor is capable of binding to a hormone response element of a wild type receptor, and
   (2) a second amino acid sequence which is positioned at the carboxy-terminal end of the DNA-binding domain, wherein said second sequence is a polypeptide which has at least about 90% as many amino acids as the ligand binding domain of the carboxy-terminal portion of said wild type receptor; wherein said polypeptide has less than about 60% amino acid identity relative to the carboxy-terminal domain of said wild type receptor over either:
   (a) the entire length of said polypeptide, if shorter than the carboxy-terminal domain of said wild type receptor, or
   (b) any segment of said polypeptide having the same length as the carboxy-terminal domain of said wild type receptor;
   wherein said chimeric receptor represses transcription from a promoter normally transrepressed by said wild type receptor.

17. A recombinant DNA encoding a trans-repressing chimeric receptor of the steroid/thyroid superfamily of receptors; wherein said receptor comprises:

(1) a first amino acid sequence which is a DNA-binding domain, through which said chimeric receptor is capable of binding to a hormone response element of a wild type receptor, and
(2) a second amino acid sequence which is positioned at the carboxy-terminal end of the DNA-binding domain, wherein said second sequence is a polypeptide which has at least about 90% as many amino acids as the ligand binding domain of the carboxy-terminal portion of said wild type receptor; wherein said polypeptide has less than about 60% amino acid identity relative to the carboxy-terminal domain of said wild type receptor over either:
  (a) the entire length of said polypeptide, if shorter than the carboxy-terminal domain of said wild type receptor, or
  (b) any segment of said polypeptide having the same length as the carboxy-terminal domain of said wild type receptor;
wherein said chimeric receptor represses transcription from a promoter normally transrepressed by said wild type receptor.

18. An expression vector operatively harboring DNA according to claim 17.

19. A recombinant host cell transfected with an expression vector according to claim 18.

20. A cell culture comprising cells according to claim 19 and an extrinsic support medium assuring the viability of said cells.

* * * * *